United States Patent
Bhushan et al.

(10) Patent No.: US 11,776,173 B2
(45) Date of Patent: Oct. 3, 2023

(54) GENERATING REFORMATTED VIEWS OF A THREE-DIMENSIONAL ANATOMY SCAN USING DEEP-LEARNING ESTIMATED SCAN PRESCRIPTION MASKS

(71) Applicant: GE Precision Healthcare LLC, Milwaukee, WI (US)

(72) Inventors: Chitresh Bhushan, Glenville, NY (US); Dattesh Dayanand Shanbhag, Bengaluru (IN); Rakesh Mullick, Bangalore (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 213 days.

(21) Appl. No.: 17/307,517

(22) Filed: May 4, 2021

(65) Prior Publication Data
US 2022/0358692 A1    Nov. 10, 2022

(51) Int. Cl.
*G06T 11/00*    (2006.01)
*G06T 7/80*    (2017.01)
(Continued)

(52) U.S. Cl.
CPC ............ *G06T 11/008* (2013.01); *A61B 5/055* (2013.01); *A61B 5/742* (2013.01); *G06T 7/0012* (2013.01);
(Continued)

(58) Field of Classification Search
CPC ....... G06T 11/008; G06T 7/0012; G06T 7/11; G06T 7/80; G06T 2207/10072;
(Continued)

(56) References Cited

U.S. PATENT DOCUMENTS 9,824,492 B2 * 11/2017 Peterson ................. G06T 19/20
10,460,208 B1    10/2019 Zhan et al.
(Continued)

FOREIGN PATENT DOCUMENTS

EP    3608871 B1    9/2021

OTHER PUBLICATIONS

Anjany Sekuboyina et al: "Verse: A Vertebrae Labelling and Segmentation Benchmark", arxiv.org, Cornell University Library, 201 OLIN Library Cornell University Ithaca, NY 14853, Jan. 24, 2020 (Jan. 24, 2020), XP081585806, the whole document.
(Continued)

*Primary Examiner* — Molly Wilburn
(74) *Attorney, Agent, or Firm* — Amin, Turocy & Watson, LLP

(57) ABSTRACT

Techniques are described for generating reformatted views of a three-dimensional (3D) anatomy scan using deep-learning estimated scan prescription masks. According to an embodiment, a system is provided that comprises a memory that stores computer executable components, and a processor that executes the computer executable components stored in the memory. The computer executable components comprise a mask generation component that employs a pre-trained neural network model to generate masks for different anatomical landmarks depicted in one or more calibration images captured of an anatomical region of a patient. The computer executable components further comprise a reformatting component that reformats 3D image data captured of the anatomical region of the patient using the masks to generate different representations of the 3D image data that correspond to the different anatomical landmarks.

20 Claims, 15 Drawing Sheets
(7 of 15 Drawing Sheet(s) Filed in Color)

(51) Int. Cl.
  *G06T 7/11* (2017.01)
  *G06V 10/25* (2022.01)
  *A61B 5/055* (2006.01)
  *A61B 5/00* (2006.01)
  *G06T 7/00* (2017.01)

(52) U.S. Cl.
  CPC ............... *G06T 7/11* (2017.01); *G06T 7/80* (2017.01); *G06V 10/25* (2022.01); *G06T 2207/10072* (2013.01); *G06T 2207/20081* (2013.01); *G06T 2207/30016* (2013.01)

(58) Field of Classification Search
  CPC . G06T 2207/20081; G06T 2207/30016; G06T 2207/10081; G06T 2207/10088; G06T 2207/20084; G06T 2207/30008; G06T 2210/41; G06T 19/00; G06T 15/08; A61B 5/055; A61B 5/742; G06V 10/25
  See application file for complete search history.

(56) References Cited

U.S. PATENT DOCUMENTS

| | | |
|---|---|---|
| 2016/0328855 A1 | 11/2016 | Lay |
| 2018/0228460 A1 | 8/2018 | Singh |
| 2019/0021677 A1* | 1/2019 | Grbic ............... G06F 18/24 |
| 2019/0216409 A1* | 7/2019 | Zhou ............... A61B 6/032 |
| 2021/0397886 A1* | 12/2021 | Chen ............... G16H 50/20 |

OTHER PUBLICATIONS

EP patent application 22171073.4 filed May 2, 2022—extended Search Report dated Sep. 22, 2022; 9 pages.
Polzin Jason: "Intelligent Scanning Using Deep Learning for MRI-TensorFlow—Medium", medium.com, Mar. 1, 2007 (Mar. 1, 2007), pp. 1-8, XP055643214, Retrieved from the Internet: URL:https://medium.com/tensorflow/intelligent-scanning-using-deep-learning-for-mri-3 6dd620882c4 [retrieved on Nov. 15, 2019] figures 1-5 chapters: Introduction—The Solution; p. 1-p. 6.

* cited by examiner

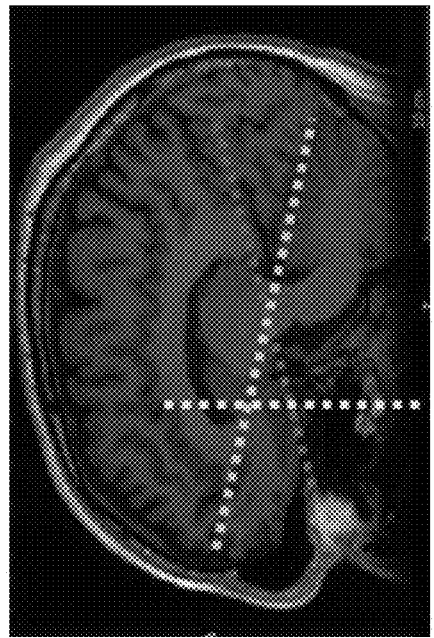
FIG. 2

FIG. 7B

GENERATING REFORMATTED VIEWS OF A THREE-DIMENSIONAL ANATOMY SCAN USING DEEP-LEARNING ESTIMATED SCAN PRESCRIPTION MASKS

TECHNICAL FIELD

This application relates to medical image processing and more particularly to generating reformatted views of a three-dimensional (3D) anatomy scan using deep-learning estimated scan prescription masks.

BACKGROUND

In clinical imaging, there is often a need to obtain images that show a contiguous view of several desired anatomies. For example, in a brain exam of an Alzheimer's disease patient, several views of the cerebral cortex may be needed to assess the patient's condition such as a contiguous view of the hippocampus, as well as a contiguous view of frontal lobe aligned with the mid-sagittal plane, the anterior commissure and the posterior commissure. Similarly, continuous view of serval anatomical landmarks are generally needed for an Optic neuritis patient, including the optic nerve, the optic trac, the optic chiasm, the optic radiation, the thalamus and the visual cortex.

Two of the most common clinical imaging techniques for obtaining a continuous view of an anatomical landmark include magnetic resonance imaging (MRI) and computed tomography (CT). These imaging procedures require acquisition of several high-resolution two-dimensional (2D) images, where each 2D image is aligned with the same anatomical landmark and captured at different points along the same acquisition plane. This approach requires repetitive scanning of the same organ from different acquisition planes to acquire different scans that respectively provide continuous views with respect to the different landmarks, a process that significantly increases scan time. Moreover, in the context of MRI, multiple contrasts images are acquired for clinical prognosis and each image is acquired separately, further increasing the scan time. Alternatively, technicians can acquire a higher resolution 3D data stack which is then reformatted manually for a desired landmark on separate imaging console.

In both scenarios, the quality of contiguous view of the anatomy is sensitive to the graphical prescription or reformatting program used and the skill of technician performing the task. For example, a small error (e.g., 3-5 degrees) in graphical prescription can lead to incorrect diagnosis or repeated scan. In the case of reformatting a 3D stack data for the desired landmark, non-familiarity with the landmark can be time-consuming or frustrating for the technician and may not be repeatable in serial scans. Accordingly, there is a strong need for more efficient clinical imaging techniques to obtain quality images providing continuous views of different anatomical landmarks of interest.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are provided that facilitate acquiring anatomy specific 3D imaging data and/or generating reformatted views of a 3D anatomy scan using deep-learning estimated scan prescription masks.

According to an embodiment, a system is provided that comprises a memory that stores computer executable components, and a processor that executes the computer executable components stored in the memory. The computer executable components comprise a mask generation component that employs a pre-trained neural network model to generate masks for different anatomical landmarks depicted in one or more calibration images captured of an anatomical region of a patient. The computer executable components further comprise a reformatting component that reformats 3D image data captured of the anatomical region of the patient using the masks to generate different representations of the 3D image data that correspond to the different anatomical landmarks. In this regard, the masks respectively provide an anatomical frame of reference for the different anatomical landmarks as depicted in the 3D image data. The one or more calibration images can include images that have a lower resolution relative to the 3D image data, such as 2D tri-planar localizer or scout images or low resolution 2D or 3D coil sensitivity images in the context of MRI.

In some implementations, the different representations comprise synthetic 2D images generated from the 3D image data. In other implementations, the different representations comprise synthetic 3D images generated from the 3D image data. In various embodiments, the 3D image data was captured along with anatomy specific region and/or a first scan plane, wherein different anatomical landmarks comprise one or more second scan planes that are different than the first scan plan, and wherein the different representations provide perspectives of the 3D image data generated from the one or more second scan planes. Additionally, or alternatively, the different anatomical landmarks comprise one or more anatomical structures and wherein the different representations provide perspectives of the three-dimensional image data relative to the one or more anatomical structures. With these embodiments, the different anatomical landmarks comprise can comprise planar and non-planar anatomical structure.

The computer executable components may further compromise a quantification component that quantifies one or more geometric or visual properties associated with one or more of the different anatomical landmarks using the masks and the three-dimensional image data. The computer executable components may further compromise an anomaly detection component that evaluates presence of one or more anomalies associated with the one or more of the different anatomical landmarks based on the one or more geometric and visual properties using machine learning and artificial intelligence techniques.

In some embodiments, elements described in the disclosed systems can be embodied in different forms such as a computer-implemented method, a computer program product, or another form.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 presents example brain scan calibration data (2D three-plane localizer) and corresponding masked calibration data in accordance with one or more embodiments of the disclosed subject matter.

FIGS. 7A and 7B provides an example dashboard with reformatted brain scan image data according to different scan-plane masks in accordance with one or more embodiments of the disclosed subject matter.

DETAILED DESCRIPTION

Figure 1:
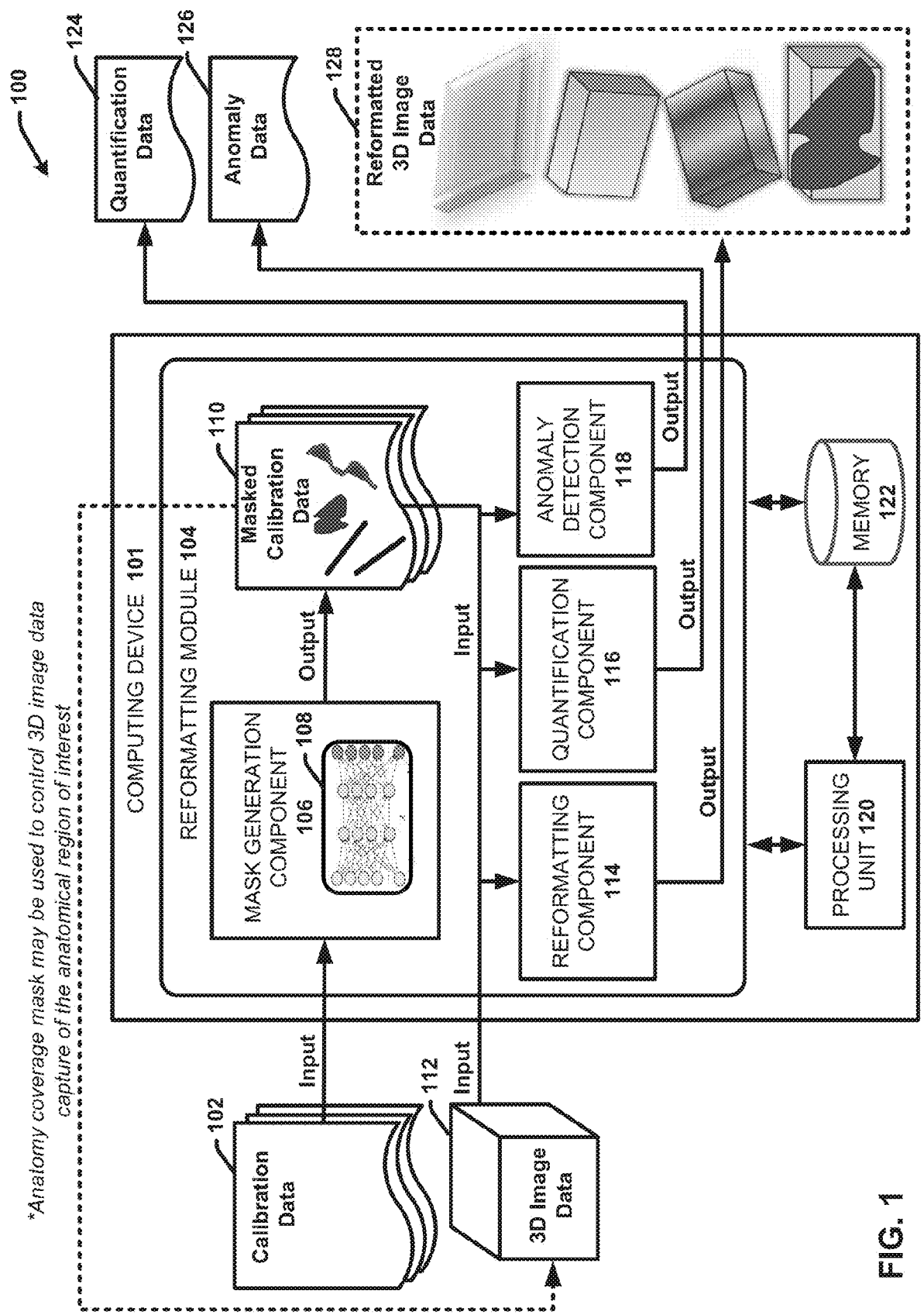
FIG. 1 illustrates a block diagram of an example, non-limiting system that facilitates generating reformatted views of a 3D anatomy scan using deep-learning estimated scan prescription masks in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate generating reformatted views of a 3D anatomy scan using deep-learning estimated anatomy coverage and scan prescription masks. For example, the 3D anatomy scan can include an MRI scan, a CT scan or the like, captured of an anatomical region of interest using the coverage mask in a patient along a single scan-plane or in isotropic resolution manner, and the reformatted views can provide different perspectives of the MRI or CT volume image from different scan-planes.

In this regard, traditional MRI and CT scans are generally performed according to manual prescriptions by specially trained technologists. For instance, the determination of the location, size, and orientation of a scanning volume requires detailed input and adjustments by a technologist. A typical scanning session begins with the acquisition of a localizer or pilot scan, which provides an overview of the major anatomical features of a patient's organ or region of interest to be scanned. The technologists then use the pilot scan to visually and manually determine the location and orientation of the scan-planes for the subsequent series of high-resolution scans.

The disclosed techniques leverage a pre-trained neural network model developed to automate this scanning process for routine to challenging set-ups. This neural-network model uses deep learning to automatically identify anatomical structures, their coverage and their orientation to prescribe slice locations, and the angle of those slices. The model automatically aligns the scan prescription to anatomical references. In various embodiments, different models can be tailored to different organs and/or anatomical parts of interested.

The disclosed techniques leverage these neural network models to automatically determine the organ descriptive and prescriptive masks using deep learning and localizer or scout images or coil sensitivity data only. In one or more embodiments, the neural network model is used to estimate arbitrary shaped scan prescription masks using deep learning from coarse low-resolution calibration images (e.g., tri-planar localizer images, scout images, or the like) without need of any additional high-resolution images. For example, the scan prescription masks can relate to different scan-planes, organ surfaces, anatomical landmarks, surrogates, or the like. In this regard, the scan prescription masks provide anatomical frame of reference for soft-tissue and other anatomical structures.

The disclosed techniques further employ these scan prescription masks to reformat a single high-resolution 3D scan image relative to the corresponding masked scan-planes and/or anatomical landmarks. This allows for any desired complex landmark visualization to be generated from a single 3D scan retrospectively without the need to reacquire again for individual landmarks or soft tissue. This standardization significantly reduces scan time, especially in MR where 2D/3D imaging oriented to individual landmarks is still vague.

In addition, the disclosed techniques can be used to estimate any arbitrarily shaped mask from localizer data, including curved or non-planar masks. Curved planar or curvilinear reformatting of the anatomical 3D image data can further be performed using these curved/non-planar masks to guide navigation, organ shape standardization and surgery decisions. Various properties of the curved planar masks can also be quantified to guide therapy device selection and diagnostic decisions.

For example, in context of organs with curvature (e.g., spine, airways, cardiac structures, blood vessels etc.), it is helpful in many clinical scenarios (e.g., aneurysm evaluation, diagnosis of dysplastic lesions in brain, neurosurgical planning, etc.) to perform curved planar reformatting to provide a contiguous visualization of the structure. This helps in better understanding of topographic relations between lesions and structures and help detect subtle abnormalities or standardization (e.g., navigation of the spine in 3D space). The quantification of these curved planar masks can also help in guiding interventional therapy device selection such as appropriate catheter/guidewire based on tortuosity. In effect, this obviates the current approach of complex mathematical modeling of such structures and facilitates accurate estimation of properties such as tortuosity and size. These quantifiable properties can in turn be also used for tracking disease progression using longitudinal scans.

Moreover, the standardization provided using an automated method ensures that post-processing tasks (e.g., organ segmentation, lesion segmentation, classification, etc.) using such data can be more robust since a big variation in data form across the sites or even a single site comes from topographical variations in anatomical data.

The types of medical images processed/analyzed using the techniques described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MR) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MR capture modality, a US capture modality, a CD capture modality, a PET capture modality, a SPECT capture modality, a NM capture modality, and the like.

As used herein, a "3D image" refers to digital image data representing an object, space, scene, and the like in three dimensions, which may or may not be displayed on an interface. 3D images described herein can include data representing positions, geometric shapes, curved surfaces, and the like. In an aspect, a computing device, such as a graphic processing unit (GPU) can generate a 3D image based on the data, performable/viewable content in three dimensions. For example, a 3D image can include a collection of points represented by 3D coordinates, such as points in a 3D Euclidean space (e.g., a point cloud). The collection of points can be associated with each other (e.g., connected) by geometric entities. For example, a mesh comprising a series of triangles, lines, curved surfaces (e.g. non-uniform rational basis splines ("NURBS")), quads, n-grams, or other geometric shapes can connect the collection of points. In an aspect, portions of the mesh can include image data describing texture, color, intensity, and the like.

In various embodiments, captured 2D images (or portions thereof) can be associated with portions of the mesh. A 3D image can thus be generated based on 2D image data, 2D sensory data, sensory data in combination with raw 2D data, 3D spatial data (e.g., spatial depth and distance information), computer generated positional data, and the like. In an aspect, data used to generate 3D images can be collected from scans (e.g., utilizing sensors) of real-world scenes, spaces (e.g., houses, office spaces, outdoor spaces, etc.), objects (e.g., furniture, decorations, goods, etc.), anatomical regions of the body, and the like. Data can also be generated based on computer implemented 3D modeling systems.

In some embodiments, a 3D image can be or include a 3D volume image that provides a 3D representation or model of an object or environment generated from a plurality of 2D images captured at different points along the same acquisition scan-plane. For example, a CT volume image can be or correspond to a 3D representation of an anatomical region of a patient generated/computed from a series of CT scan slices captured at different points along a same acquisition scan-plane. Similarly, an MRI volume image can be or correspond to a 3D representation of an anatomical region of a patient generated/computed from a series of MRI scan slices captured at different points along a same acquisition plane. In this regard, as applied to medical imaging, a 3D image can be or include a 3D volume image of anatomical region of a patient.

In this regard, a 3D medical image refers to a 3D representation of an anatomical region of a patient. In some implementations, a 3D medical image can be captured in 3D directly by the acquisition device and protocol. In other implementations, a 3D medical image can comprise a generated image that was generated from 2D and/or 3D image data captured of the anatomical region of the patient. Some example 3D medical images include 3D volume images generated from CT image data, and MRI image data.

It is noted that the terms "3D image," "3D volume image," "volume image," "3D model," "3D object,", "3D reconstruction," "3D representation," "3D rendering," and the like are employed interchangeably throughout, unless context warrants particular distinctions among the terms. It should be appreciated that such terms can refer to data representing an object, an anatomical region of the body, a space, a scene, and the like in three dimensions, which may or may not be displayed on an interface. The terms "3D data," and "3D image data" can refer to a 3D image itself, data utilized to generate a 3D image, data describing a 3D image, data describing perspectives or points of view of a 3D image, capture data (e.g., sensory data, images, etc.), meta-data associated with a 3D image, and the like. It is noted that the term "2D image" as used herein can refer to data representing an object, an anatomical region of the body, a space, a scene, and the like in two dimensions, which may or may not be displayed on an interface.

The term "native" image is used herein to refer to an image in its original capture form and/or its received form prior to processing by the disclosed systems. In this regard, a native 3D image refers to a 3D image in its received state prior to reformatting using one or more estimated scan prescription masks. For example, a native 3D image can include a received 3D volume image, such a s CT volume image or an MRI volume image. The term "synthetic" image is used herein to distinguish from native images and refers to an image generated or derived from a native image using one or more reformatting processing techniques disclosed herein. In various embodiments, a synthetic image refers to a reformatted 2D or 3D image generated from a native 3D volume image using the disclosed reformatting techniques.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system that facilitates acquisition of anatomy specific 3D and then generating reformatted views of a 3D anatomy scan using deep-learning estimated coverage and scan prescription masks in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a computing device 101 that comprises a reformatting module 104 that can be and/or include various computer executable components. In the embodiment shown, these computer executable components include a mask generation component 106, a reformatting component 114, a quantification component 116 and an anomaly detection component 118. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 122 of the computing device 101 which can be coupled to processing unit 120 for execution thereof. Examples of said and memory and processor as well as other suitable computer or computing-based elements, can be found with reference to FIG. 14, and can be used in connection with implementing one or more of the systems or components shown and described in connection with FIG. 1 or other figures disclosed herein.

System 100 further includes calibration data 102, 3D image data 112 and reformatted 3D image data 128. In various embodiments, the 3D image data 112 can correspond to 3D anatomy scan data captured of a patient's anatomy from a single acquisition scan-plane. For example, the 3D image data 112 can correspond to an MR scan, a CT scan or the like captured of a particular organ or anatomical body part of interest from one scan prescription plane. The anatomical region of interest can be chosen using the coverage mask also provided by the deep learning mask generation component 106. With these embodiments, the 3D image data 112 can comprise a plurality of high-resolution (e.g., isotropic) 2D images corresponding to different scan slices captured at different points along the acquisition axis. For example, as applied to MRI, in some implementations the 3D image data 112 can typically include isotropic images captured at a voxel/resolution size of about 0.5×0.5×0.5 $mm^3$. The combined 2D images respectively form a 3D volume image of the anatomy captured.

The calibration data 102 can include one or more calibration images captured of the same patient's anatomy in association with capture of the 3D image data 112. These calibration images can include one or more low-resolution images captured of the patient's region of interest to be scanned prior to capture of the subsequent high-resolution (e.g., isotropic) 3D image data 112 of the region of interest that are generally used to position/align the scanner relative to a desired scan prescription plane for which the 3D image data 112 is captured. In this regard, the calibration images can have a lower resolution/image quality relative to the 3D image data 112 yet depict the same or wider region of interest.

For example, in some implementations in which the 3D image data 112 corresponds to an MRI scan or a CT scan, the calibration images can include localizer images, such as three-axis (or tri-planar) localizer images the provide a view of patient's anatomy/organ in the three scanner-frame axes. Localizer images are 2D or 3D low resolution mages used to provide initial guidance to operator. These are common to both CT and MRI. The three axes can vary depending on the anatomy/organ to be scanned and/or the landmark anatomical structures of interest. For example, as applied to brain scans, the three axes could include the axial, sagittal and coronal axes. In other implementations, the three axes can include relative x-axis, y-axis and z-axis of the 3D bounding box used to define the 3D imaging coverage volume for which the subs-sequent high-resolution scans are captured. Localizer images, (also called scout images in CT), are used in MR and CT studies to identify the relative anatomical position of a collection of cross-sectional images. A localizer image can be acquired as a separate image, as is often done for CTs, or it can be dynamically generated, as is done for MRIs. Some example localizer images are presented in FIGS. 2-3 and discussed in greater detail infra. The calibration images may also include coil sensitivity images that are specific to MRI. These are typically not shown or used by technologists for planning Some example coil sensitivity images are shown in FIG. 4 and discussed in greater detail infra. The terms "localizer image," "scout image," "calibration image," "pilot image," "reference image," and the like are used herein interchangeably unless context warrants particular distinction amongst the terms.

Additionally, or alternatively, the calibration data 102 can include the scan parameters regarding the scanner localization for the capture of the 3D image data 112. For example, such additional scan parameters can include, but are not limited to, the field of view (FOV), the relative position and dimensions of the 3D bounding box, the relative position and orientation of the prescription scan-plane used to capture the 3D image data 112 (e.g., relative to the 3D bounding box and/or one or more anatomical landmarks), and the scanner capture position and orientation used to capture the 3D image data 112.

The reformatting module 104 can provide for retrospectively processing the 3D image data 112 using the calibration data 102 to generate reformatted views of the 3D image data 112 with respect to different scan-planes and/or different anatomical landmarks of interest. The reformatted views can essentially correspond to slicing of the 3D image data 112 along any desired plane other than the capture scan-plane. In this regard, the reformatted views can provide continuous views (e.g., a series of high-resolution 2D images/scan slices) of the 3D image data 112 aligned relative to different anatomical features of interest. In the embodiment shown, these reformatted views are represented as reformatted 3D image data 128. To facilitate this end, the reformatting module 104 can include mask generation component 106 and reformatting component 114.

The mask generation component 106 can processes the calibration data 102 using one or more pre-trained deep learning networks 108 to estimate the relative position and/or shape of defined anatomical landmarks and/or scan-planes depicted in the one or more calibration images. The mask generation component 106 can further generate masks for the anatomical landmarks and/or scan-planes on the one or more calibration images, resulting in transformation of the calibration images into masked calibration data 110. The anatomical landmarks can include planar and non-planar structures anatomical structures (e.g., organs, soft tissue structures, bones, ligaments, vessels, etc.), positions/points/planes between two or more anatomical structures, surfaces of anatomical structures, and the like. For example, in some implementations, the masks can include segmentation masks defining an organ or anatomical landmark structure of interest. These segmentation mask can include planar masks as well as non-planar marks for curved anatomical structures (e.g., curved vessels, spine, etc.). The masks can also include scan-plane lines marking different scan-planes as aligned with one or more anatomical landmarks.

In this regard, in some implementations the masked calibration data 110 can correspond to one or more calibration images with graphical mask overlays provided thereon, wherein the graphical mask overlays define the shape and position of an anatomical landmark and/or a scan-plan relative to an anatomical landmark. Additionally, or alternatively, the mask generation component 106 can generate localization parameters defining the relative position and/or geometry of the anatomical landmarks and/or scan-planes in the one or more calibration images and/or within the 3D image data 112. For example, the localization parameters can define the relative positions of different scan-planes aligned with different anatomical landmarks in the 3D image data 112, define the relative center-points/positions of different anatomical landmarks in the 3D image data 112, define the relative 2D and/or 3D shape and position of different anatomical landmarks in the 3D image data 112 and the like.

In some embodiments, the masked calibration data 110 can also include an anatomy coverage mask that defines a 3D volume of the anatomical region of interest for which the 3D image data 112 is captured. For example, the anatomy coverage mask can define the 3D bounding box of the coverage area for which to capture the 3D image data 112. In this regard, the mask generation component 106 can employ one or more pre-trained neural network models 108 to generate the anatomy coverage mask based on the calibration data 102. This anatomy coverage mask can be generated prior to the capture of the 3D image data 112 and used to control the capture of the 3D image data 112 such that only the desired anatomical region of interest is captured in the high-resolution 3D image data. This helps in improving the time efficiency of 3D acquisition.

FIG. 2 presents example brain scan calibration data and corresponding masked calibration data in accordance with one or more embodiments of the disclosed subject matter. In this example, the calibration data includes 2D tri-planar (e.g., axial, coronal, and sagittal planes) localizer images 202 captured of the brain in association with performance of an MRI scan of the brain. The example masked calibration data includes a masked image 204 marked with different scan-plane masks corresponding to projected planes for different anatomical landmarks of interest. In this example, the scan-plane masks are projected onto the axial localizer image and provide the relative reference planes for the anterior commissure (AC)-posterior commissure (PC) plane (e.g., the superior edge of the AC and the inferior edge of the PC, referred to as the ACPC plane/line), the hippocampus plane and pituitary plane. With reference to FIGS. 1 and 2, in various embodiments, the localizer images 202 can correspond to the calibration data 102 and the masked image 204 can correspond to the masked calibration data.

Figure 3:
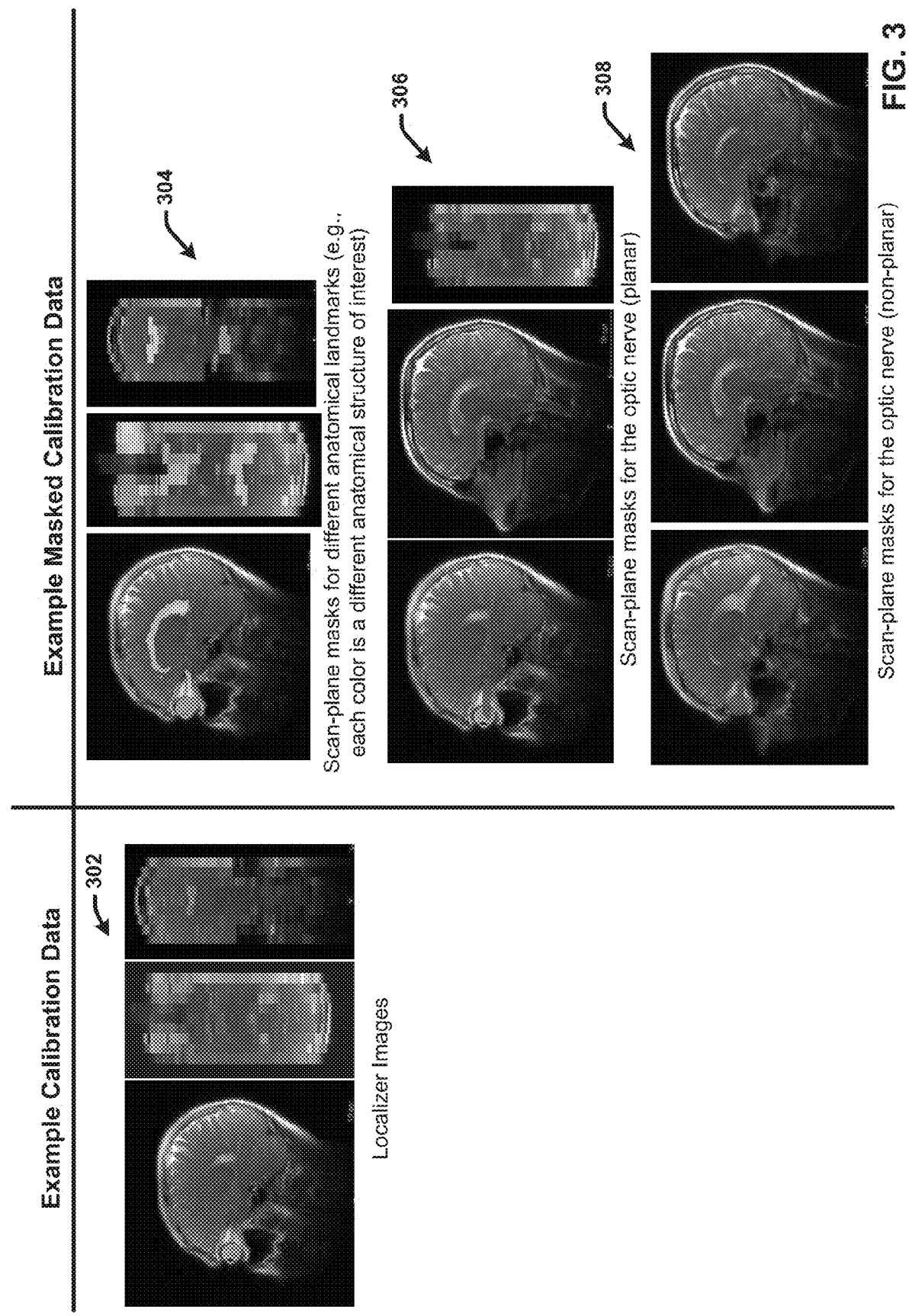
FIG. 3 presents additional example brain scan calibration data (2D three-plane localizer images) and corresponding masked calibration data in accordance with one or more embodiments of the disclosed subject matter.
Figure 4:
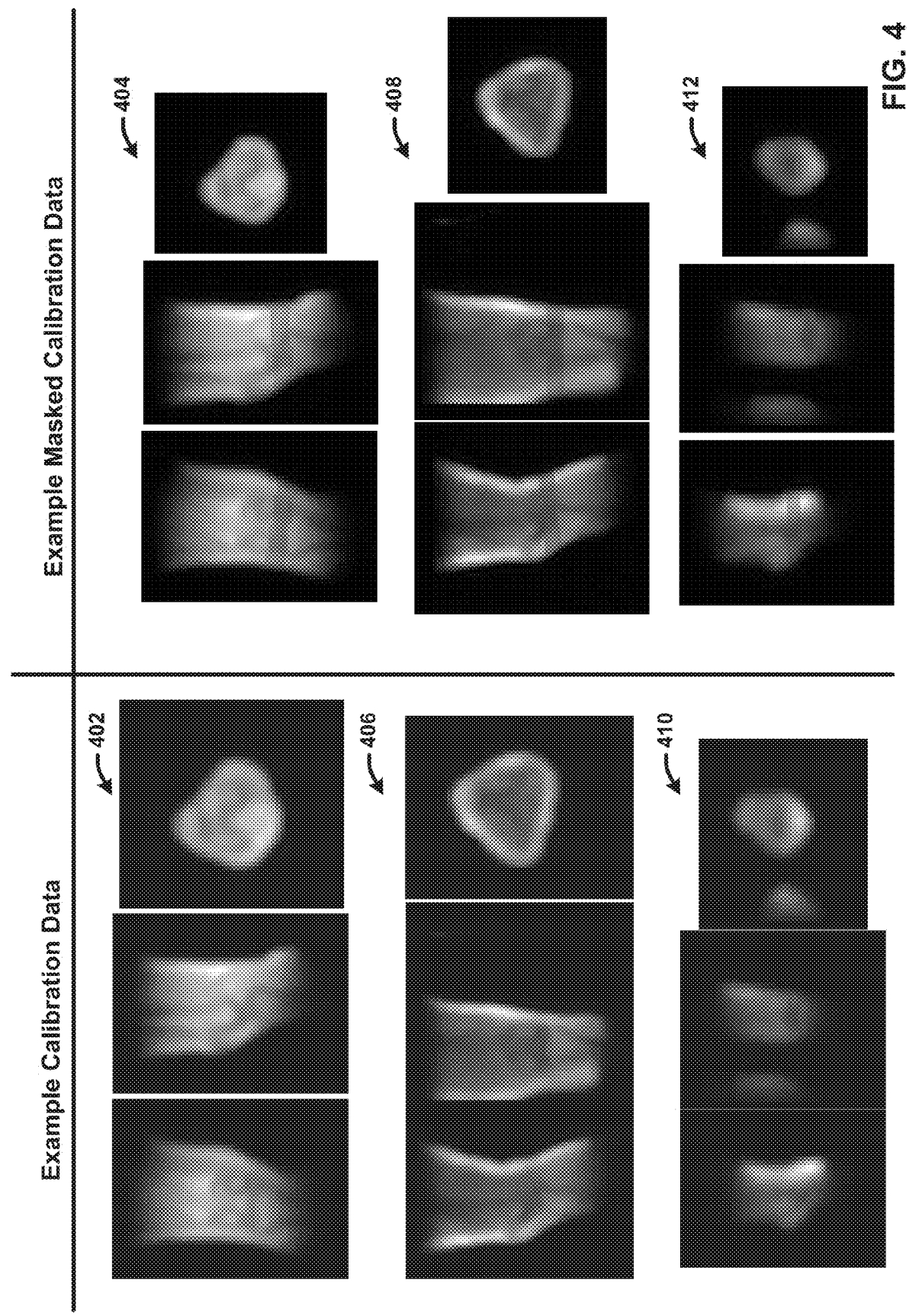
FIG. 4 presents example knee scan calibration data (3D body coil sensitivity scan images) and corresponding masked calibration data in accordance with one or more embodiments of the disclosed subject matter.

FIG. 3 presents additional example brain scan calibration data and corresponding masked calibration data in accordance with one or more embodiments of the disclosed subject matter. In this example, the calibration data also includes 2D tri-planar localizer images 202 captured of the brain in association with performance of an MRI scan of the brain. The example masked calibration data includes different sets of masked localizer images with scan-plane masks corresponding to different anatomical landmarks of interest. In this example, the scan-plane masks define the relative position and geometry of defined anatomical structures. In particular, the masked images 304 provide scan plane masks for different anatomical landmarks of interest, wherein each color correspond to a different anatomical structure of interest. The masked images 306 provide planar scan-plan masks for the optic nerve, and the masked images 308 provide non-planar scan plane masks for the optic nerve. With reference to FIGS. 1 and 3, in various embodiments, the localizer images 302 can correspond to the calibration data 102 and the masked images 302, masked images 306 and masked images 308 can correspond to the masked calibration data 110.

FIG. 4 presents example knee scan calibration data and corresponding masked calibration data in accordance with one or more embodiments of the disclosed subject matter. In this example, the calibration data includes three sets of low-resolution 3D coil sensitivity images captured of a patient' knee in association with performance of an MRI scan of the knee. The example masked calibration data includes corresponding sets of masked images marking the meniscus plane in each of the calibration images. For example, masked images 404 mark the meniscus plane on calibration images 402, masked images 408 mark the meniscus plane on calibration images 406 and masked images 412 mark the meniscus plane on calibration images 410. With reference to FIGS. 1 and 4, in various embodiments, the calibration images 402, 406 and 410 can correspond to the calibration data 102 and the masked images 404, 408 and 412 can correspond to the masked calibration data 110.

With reference again to FIG. 1, as noted above, the mask generation component 106 can employ one or more deep learning networks 108 to generate the masked calibration data 110 from the calibration data 102. These one or more deep learning networks 108 can be configured to estimate scan-plane masks and/or localization parameters (e.g., relative to the calibration images and/or the 3D image data 112) for defined anatomical landmarks for a particular anatomical organ or region of interest, such as the brain, the knee, the spine, the chest and various other anatomical organs/regions of interests. In this regard, in some embodiments, the one or more deep learning networks 108 can include a separate neural network model trained for each anatomical organ/region of interest.

The specific scan-plane masks that the neural network model is trained to identify and define for a specific organ/ anatomy and define can vary. For example, as applied to the brain, the neural network model can be configured to identify and define scan-plane masks and/or localization parameters for a variety of different anatomical landmarks and reference planes, including but not limited to, the mid-sagittal plane (MSP), the ACPC plane, the hippocampus, the optic nerve, the obits, the internal auditory canal (IAC), the brainstem vertical plane, the orbitomeatal plane, the Reid's baseline, the subcallosal line, the supraorbital-meatal line, and the tuberculum sellae and the external occipital protuberance line. In some embodiments, the one or more deep learning networks 108 can include separate networks/models trained to identify/defined each particular anatomical landmark/scan-plane. Additionally, or alternatively, the one or more deep learning networks 108 can provide for multi-plane estimation using a single network.

The architecture of the one or more deep learning networks 108 can vary. In some embodiments, the one or more deep learning networks can employ a u-net convolutional network segmentation model combined with a shape-autoencoder to generate the scan-plane masks. For example, in one implementation, instead of predicting the binary mask, the network predicts its signed distance transform and this is thresholded and run through a shape encoder to provide the binary mask.

The reformatting component 114 can reformat the 3D image data 112 using the masked calibration data 110 to generate the reformatted 3D image data 128. In particular the reformatting component 114 can map the scan-plane masks and/or localization parameters defining the relative position/geometry of the scan-plane masks in the calibration images to their relative positions/geometries in the 3D image data 112. Because the different scan-plane masks correspond to different anatomical landmarks of interest, the reformatted 3D image data 128 can respectively provide reconstructed views of the 3D image data 112 from with respect to the different anatomical landmarks. In this regard, the reformatting component 114 can employ the masked calibration data 110 to determine the relative positions and geometries of different scan-planes aligned with different anatomical landmarks and/or the relative positions and dimensions of anatomical structures within the 3D image data 112. The reformatting component 114 can further "slice" the 3D image data 112 relative to one or more of the different scan-plane masks/anatomical landmarks defined in the masked calibration data 110 to generate a continuous view of the 3D image data 112 from the perspectives of the respective scan-plan masks/anatomical landmarks.

For example, for planar mask the reformatting processing preformed by the reformatting component 114 can include slicing the 3D image data 112 (e.g., a 3D volume image of the anatomical region of interest) using the scan-plane fitted through it. Similarly, for organ masks, the reformatting component can either fit a plane relative to the organ/organ mask in the 3D image data and do the slicing along the fitted plane or perform an "unwrapping or unfolding" of the organ in the 3D image data along the skeletal axis and generate an unwrapped/planar view of the organ along the skeletal axis for presenting to the viewer. For non-planar masks, the reformatting component 114 may perform the reformatting of the 3D image data 112 projecting the curved points of the non-planar mask into a flat 2D surface by aligning the skeletal axis of the imaging plane with a specific anatomic structure corresponding to the non-planar mask (e.g. blood vessel). In this regard, the non-planar reformatting may be construed to an unwrapping or straightening the curved structure along a selected reference axis of the anatomical structure (e.g., is primary skeletal axis).

The result of the reformatting can include one or more high-resolution synthetic 2D images that correspond to regenerated slices of the 3D image data 112 as if they natively were captured with a capture position and orientation and field of view that was aligned with the corresponding scan-plan masks defined in the masked calibration data 110. In this regard, the synthetic 2D images can be viewed individually, in series (as a continuous view relative to the new scan-plane), and/or combined into a new synthetic 3D volume image.

The reformatting component 114 can also perform curved planar or curvilinear reformatting of the anatomical 3D image data 112 using curved/non-planar masks generated for curved/non-planar anatomical structures included in the 3D image data 128. For example, in context of organs with curvature (e.g., spine, airways, cardiac structures, blood vessels etc.), it is helpful in many clinical scenarios (e.g., aneurysm evaluation, diagnosis of dysplastic lesions in brain, neurosurgical planning, etc.) to perform curved planar reformatting to provide a contiguous visualization of the structure. This helps in better understanding of topographic relations between lesions and structures and help detect subtle abnormalities or standardization (e.g., navigation of the spine in 3D space). In this regard, the reformatting component 114 can generate a planar view of a non-planar anatomical structure included in the 3D image data using its corresponding non-planar mask.

Figure 5:
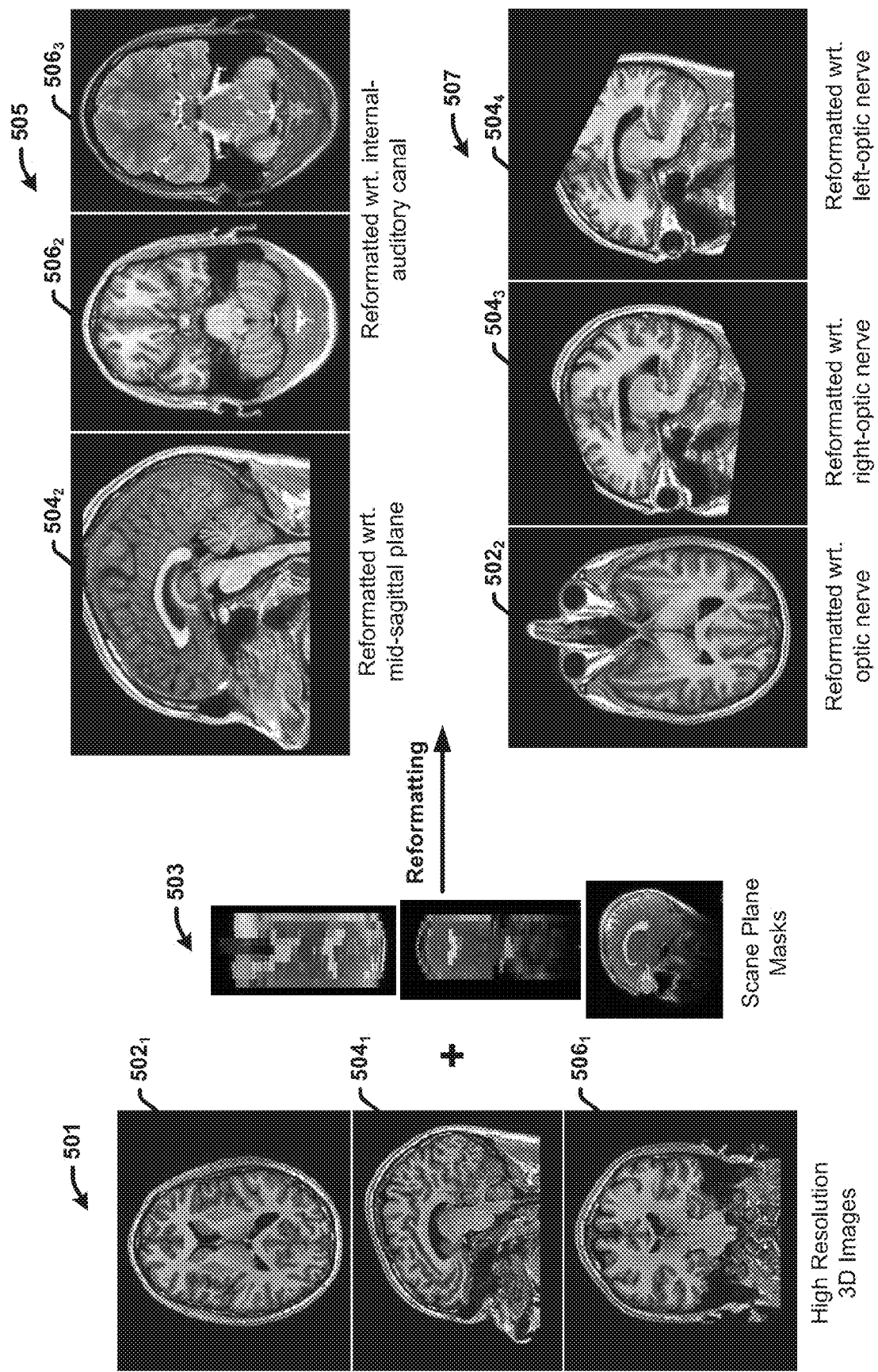
FIG. 5 presents example high-resolution 3D images of the brain and corresponding reformatted 3D images in accordance with one or more embodiments of the disclosed subject matter.

FIG. 5 presents example high-resolution 3D images of the brain and corresponding reformatted 3D images in accordance with one or more embodiments of the disclosed subject matter. In this example, images 501 correspond to high-resolution MRI images captured of the brain in association with three separate single acquisitions along a three different scan-prescription planes.

For example, image $502_1$ correspond to one high-resolution image associated with a first 3D volume image captured during a first isotropic acquisition of the brain from the axial direction. The axial acquisition looks at the brain from below in a series of high-resolution 2D images starting from the chin and moving to the top of the head Image $502_1$ provides one exemplary native image from this 3D axial brain scan. Image $504_1$ correspond to one high-resolution image associated with a second 3D volume image captured during a second isotropic acquisition of the brain from the sagittal direction. The sagittal acquisition looks at the brain from the side in a series of high-resolution 2D images starting from one ear and moving to the other Image $504_1$ provides one exemplary native image from this 3D sagittal brain scan. Image $506_1$ correspond to one high-resolution image associated with a third 3D volume image captured during a third isotropic acquisition of the brain from the coronal direction. The coronal acquisition looks at the brain from behind side in a series of high-resolution 2D images starting from the back of the head and moving to the face Image $506_1$ provides one exemplary native image from this 3D coronal brain scan.

Images 505 and 507 provide example reformatted high-resolution images that can be generated from one or more of the 3D volume images (from which images 501 were sampled) using the corresponding scan-plan masks 503. These scan-plane masks 503 are merely exemplary and in this example are intended to provide masks for the mid-sagittal pane, the internal auditory canal. In this regard, image $504_2$ provides a reformatted version of image $504_1$ with respect to the mid-sagittal plan. Image $506_2$ and image $506_3$ provide reformatted versions of image $506_1$ as reformatted with respect to the internal auditory canal. Image $502_2$ provides a reformatted version of image $502_1$ as reformatted with respect to the optic nerve. Image $504_2$ provides another reformatted version of image $504_1$ as reformatted with respect to the optic nerve from the right side, and image $504_4$ provides another reformatted vide of image $504_1$ as reformatted with respect to the optic nerve from the left.

In this example, three separate high-resolution acquisitions of the brain are provided merely for exemplary purposes. However, it is noted that only one of these acquisitions is needed to generate one 3D volume from which the different reformatted views of images 505 and 507 can be generated by the reformatting component 114. However, in some implementations, certain native acquisition planes may be better suited for generating reformatted view with respect to certain anatomical landmarks.

Figure 6:
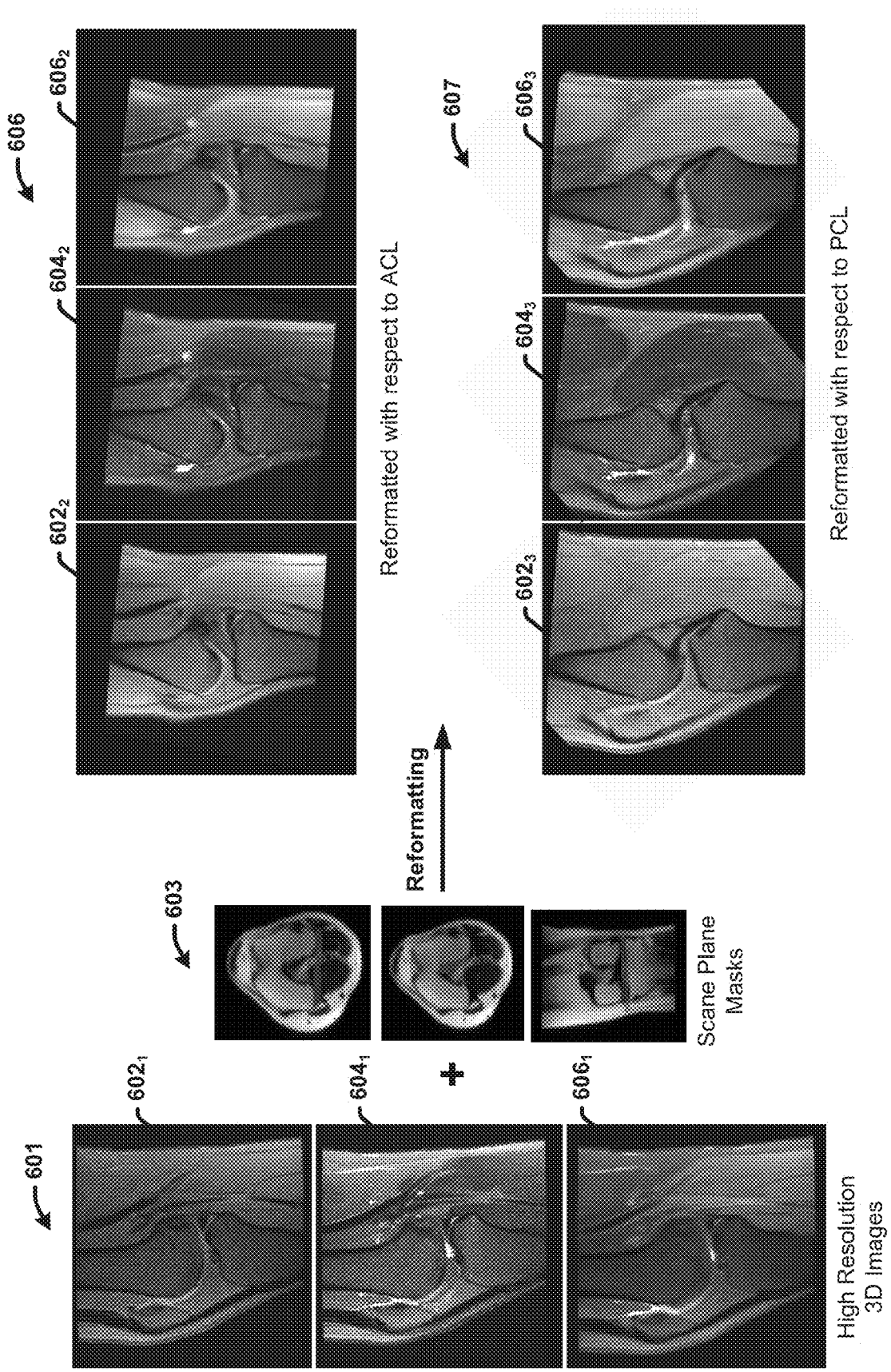
FIG. 6 presents example high-resolution 3D images of the knee and corresponding reformatted 3D images in accordance with one or more embodiments of the disclosed subject matter.

FIG. 6 presents example high-resolution 3D images of the knee and corresponding reformatted 3D images in accordance with one or more embodiments of the disclosed subject matter. In this example, images 601 correspond to high-resolution MRI images captured of the knee in association with three separate single acquisitions along the same scan-prescription plane yet with different acquisition weighting protocols.

In this regard, unlike imaging using radiation, in which the contrast depends on the different attenuation of the structures being imaged, the contrast in MRI images depends on the magnetic properties and number of hydrogen nuclei in the area being imaged. Different contrasts in the area being imaged can be selected for by running different sequences with different weightings. The main three sequences are: T1-weighted (maximum T1 contrast shown), T2-weighted (maximum T2 contrast shown), and Proton density (PD) weighting (density of hydrogen protons shown).

Image $602_1$ correspond to one high-resolution image associated with a first 3D volume image captured during a T1 acquisition of the knee Image $604_1$ correspond to one high-resolution image associated with a second 3D volume image captured during a T2 acquisition of the knee, and image $6062_1$ corresponds to one high-resolution image associated with a third 3D volume image captured during a PD acquisition of the knee.

Images 605 and 607 provide example reformatted high-resolution images that can be generated from one or more of the 3D volume images (from which images 601 were sampled) using the corresponding scan-plan masks 603. These scan-plane masks 603 are merely exemplary and in this example are intended to provide scan-plane masks for the anterior cruciate ligament (ACL) and the posterior cruciate ligament (PCL). In this regard, image $602_2$ provides a reformatted version of image $602_1$ with respect to the ACL, image $604_2$ provides a reformatted version of image $604_1$ with respect to the ACL, and image $606_2$ provides a reformatted version of image $606_1$ with respect to the ACL. Similarly, image $602_3$ provides a reformatted version of image $602_1$ with respect to the PCL, image $604_3$ provides a reformatted version of image $604_1$ with respect to the PCL, and image $606_3$ provides a reformatted version of image $606_1$ with respect to the PCL.

Figure 7A:
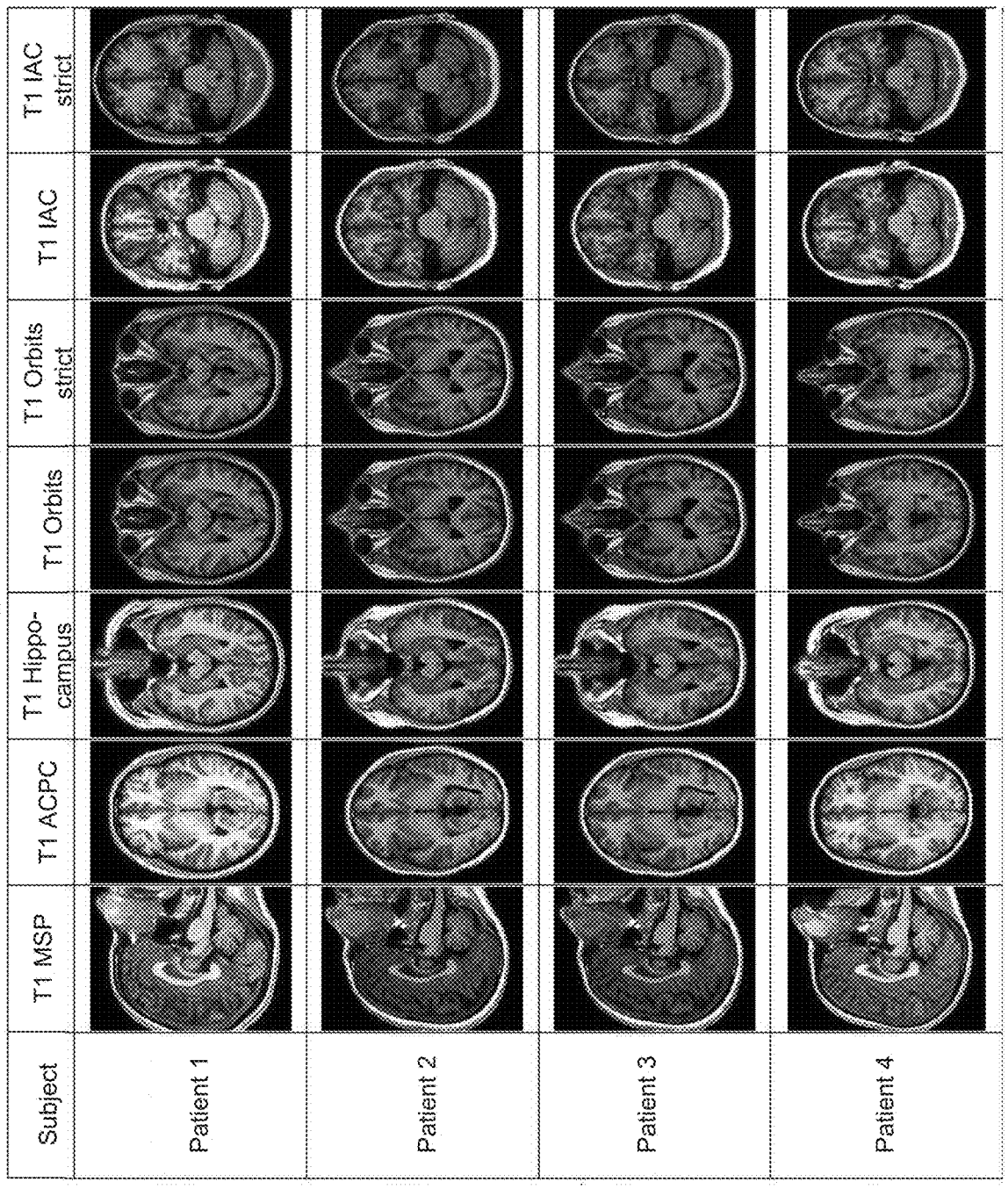
Figure 7B:
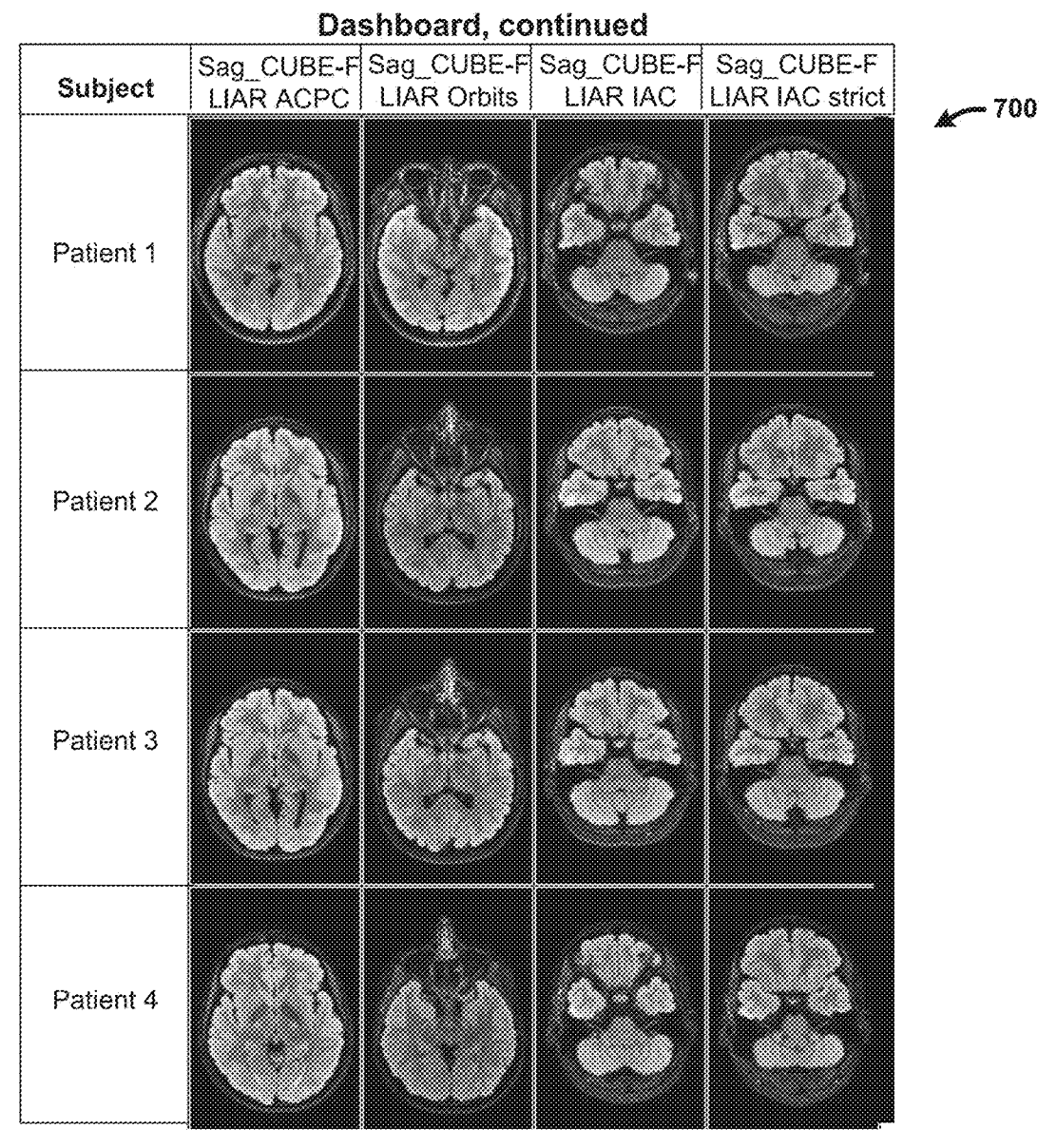

FIGS. 7A and 7B provides an example dashboard 700 with reformatted brain scan image data according to different scan-plane masks in accordance with one or more embodiments of the disclosed subject matter. Dashboard 700 provides several high-resolution 2D images of the brain for different patient. In various embodiments, each of the different views were generated from a single 3D MRI acquisition performed for each patient. The different view provide reformatted/regenerated views relative to different anatomical landmarks using corresponding scan-plane masks generated for the different anatomical landmarks using one or more calibration images captured for each patient, the mask generation component 106 and the one or more deep-learning neural networks 108.

With reference again to FIG. 1 the quantification component 116 can further determine quantifiable properties of masks generated by the mask generation component 106. For example, the quantification component 116 can determine the relative position and geometry of anatomical structures in the 3D image data using their corresponding masks. The quantification component 116 can also determine various quantifiable visual properties associated with the masks and/or masked region as mapped to the high-resolution 3D image data 112. For example, such visual properties can relate to the degree/amount of tortuosity, coloration, pixilation, coloration variation, and the like. In some implementations, the quantification component 114 can also perform pattern recognition to characterize distinct visual patterns associated with the masks and/or their corresponding anatomical structures.

In this regard, the quantification of curved/non-planar masks for curved/non-planar anatomical structures can also help in guiding interventional therapy device selection such as appropriate catheter/guidewire based on tortuosity. In effect, this obviates the current approach of complex mathematical modeling of such structures and facilitates accurate estimation of such properties. These quantifiable properties can also be for tracking disease progression using longitudinal scans based on the changes in the visual properties over time. These quantifiable properties may also be used by the reformatting component 114 in association with generating reformatted view of the anatomical structures, including one-dimensional 1D reformatted views. For example, the reformation component 114 may use information defining the thickness and/or length of a blood vessel using its corresponding mask to follow its curvilinear structure and map out its thickness and length.

The quantification component 116 can also determine measurement data regarding relative positions between structures. For example, the quantification component 116 can determine the relative-angle, distance and relative-position between two or more masks/structures (e.g., the angle between ACL and the PCL in knee, the mutual distance between AC, PC and pituitary structures, etc.). The quantification component 116 can also quantify geometric and morphological features of each (or a combination of) mask/structure (e.g., how is optic nerve bent? How long and thick is the IAC? What is the shape of meniscus (knee) or hippocampus (brain)? etc.). These quantifications can have several uses. For example, they can be used by the anomaly detection component 118 to help plan any intervention as well as used to automatically detect abnormalities (e.g., with respect to the general population and the patient's condition). With these embodiments, the anomaly detection component 118 can employ various machine learning and/or artificial intelligence techniques to detect abnormalities present in a patient's imaging data based on various quantifiable metrics determined for one or more anatomical structures based on their scan-plane masks.

The quantifiable/measurement data can also be used to define the relative "importance" of each reformatted view, which could be used to flag/raise concerns. For example, the anomaly detection component 118 can employ machine learning and/or artificial intelligence techniques to determine/infer, based on the optic nerves quantified size, that the optic nerve is unusually thick (e.g., indicative of swelling) in a particular subject. The quantification component 116 can further suggest specific reformatted views for generating based on the detected abnormality. For instance, continuing with the optic nerve swelling example, the anomaly detection component 118 can instruct the reformatting component to generate different optic nerve reformatted views for presenting to the clinician (e.g., the radiologist, the technician, etc.). Additionally, or alternatively, the anomaly detection component 118 can direct the system to render and/or place the optic nerve reformatted views in a priority viewing section/area of the rendering user interface (e.g., at the top of a visualization dashboard used to view the reformatted views).

The deployment architecture of system 100 can vary. In the embodiment shown, each of the mask generation component 106, the reformatting component 114, the quantification component 116 and the anomaly detection component 118 are included within a reformatting module 104 deployed on a computing device 101. In some implementations, the computing device 101 can include or be operatively coupled to the medical image scanning device (e.g., a CT machine, an MRI machine, etc.) that captures the calibration data 102 and the 3D image data 112. Additionally, or alternatively, the computing device 101 can include a separate device/machine (e.g., real or virtual/cloud-based) that is communicatively coupled to the imaging scanning device or an external image data storage system where the calibration data 102 and the 3D image data 112 is stored such as a Picture Archiving and Communication System (PACS) and/or a Vendor Neutral Archive (VNA). For example, the computing device 101 can be communicatively coupled to the medical image scanning device and/or the medical image storage system via one or more wired or wireless communication networks (e.g., a wide area network (WAN), a local area network (LAN), or the like). In either of these embodiments, the reformatted 3D image data 128 can be stored by the computing device 101, exported to another storage system and/or exported to visualization system where it can be viewed/displayed. Still in other embodiments, one or more components of the reformatting module 104 can be deployed at different computing devices/machines in a distributed computing environment and communicatively coupled via one or more networks. Various alternative deployment architecture variations can also be used.

Figure 8:
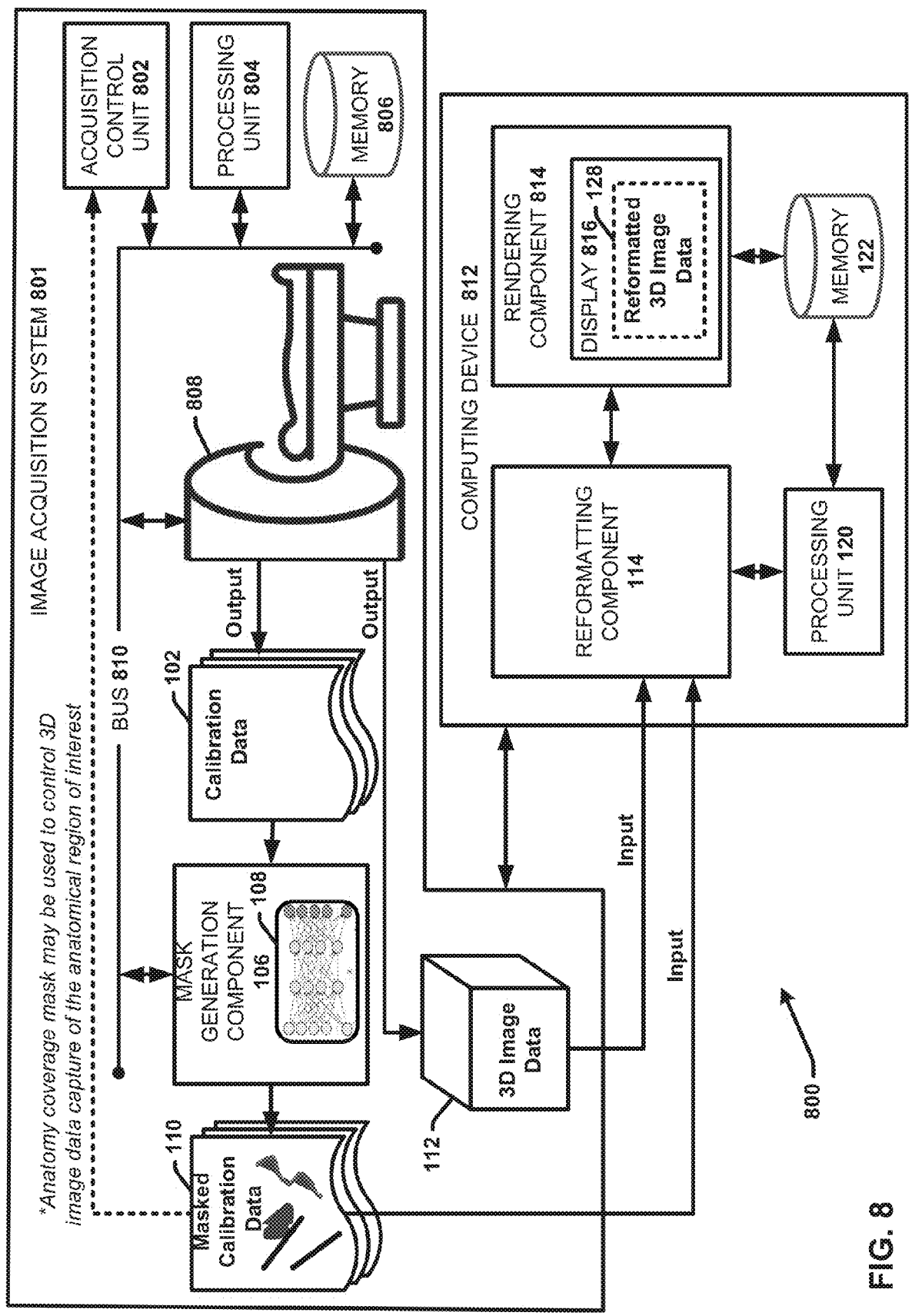
FIG. 8 illustrates a block diagram of another example, non-limiting system that facilitates acquisition and/or generating reformatted views of a 3D anatomy scan using deep-learning estimated scan prescription masks in accordance with one or more embodiments of the disclosed subject matter.

FIG. 8 illustrates a block diagram of another example, non-limiting system 800 that facilitates generating reformatted views of a 3D anatomy scan using deep-learning estimated scan prescription masks in accordance with one or more embodiments of the disclosed subject matter. System 800 provides another example deployment architecture for the mask generation component 106 and the reformatting component 114. Repetitive description of like elements employed in respective embodiments is omitted for sake of brevity.

System 800 includes an image acquisition system 801 that includes the mask generation component 106 and a computing device 812 that includes the reformatting component 114 and a rendering component 814. Although not shown, the image acquisition system 801 and/or the computing device 812 may include the quantification component 116 and the anomaly detection component 118. The image acquisition system 801 includes the medical image scanning device 808 that captures the calibration data 102 and the 3D image data 112. The image acquisition system 801 can further include computer executable components that facilitate processing the captured image data (e.g., the calibration data 102 and the 3D image data 112) and controlling the image acquisition process by the medical image scanning device 808. These computer executable components include the mask generation component 106 and acquisition control unit 802. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 806 of the image acquisition system 801 which can be coupled to processing unit 804 for execution thereof. The image acquisition system 801 can further include a system bus 810 that communicatively and operatively couples the various machine/computer executable components of system 801 to one another (e.g., the mask generation component 106, the medical image scanning device 808, the acquisition control unit 802, the processing unit 804, and the memory 806).

In one or more embodiments, the acquisition process may include capture of the calibration data 102 prior to capture of the 3D image data 112 when the patient is positioned on/withing the scanning device 808. The mask generation component 108 can process the calibration data 102 using the mask generation component 106 to generate at least some of the masked calibration data 110 prior to capture of the 3D image data 112. In particular, the mask generation component 106 can generate an anatomy coverage mask defining the 3D bounding box of the anatomical region of interest for which the subsequent high resolution 3D image data 112 of the patient will be captured. For example, the acquisition control unit 802 can control the acquisition of the 3D image data 112 the scanning device 808 based on the anatomy coverage mask by positioning and/or facilitating positioning of the patient relative to the scanning device 808 such that only the region of interest defined by the anatomy coverage mask is captured. As noted previously, this helps in improving the time efficiency of 3D acquisition process. The mask generation component 106 may further generate additional scan-plane masks (e.g., defining planar scan-planes, defining geometric shapes of anatomical structures, etc.) using the calibration data 102 prior to, during, and/or after capture of the capture of the 3D image data 112.

The image acquisition system 801 can further provide the 3D image data 112 and the mask calibration data 110 to the computing device 812 for processing by the reformatting component 114 to generate the reformatted 3D image data 128. For example, the computing device 812 and the image acquisition system 801 can be communicatively coupled via one or more wired or wireless communication networks. In this example embodiment, the reformatting component 114 can generate the reformatted 3D image data 128 using the 3D image data 112 and the masked calibration data 110 provided by the image acquisition system 801. This can be performed in real-time (e g, immediately upon generation of the 3D image data 112) and/or retrospectively (e.g., at any point thereafter). The computing device 812 can further include a rendering component 814 and a display 816 that provide for rendering the reformatted 3D image data 128 at the computing device 812 via the display 816.

Figure 9:
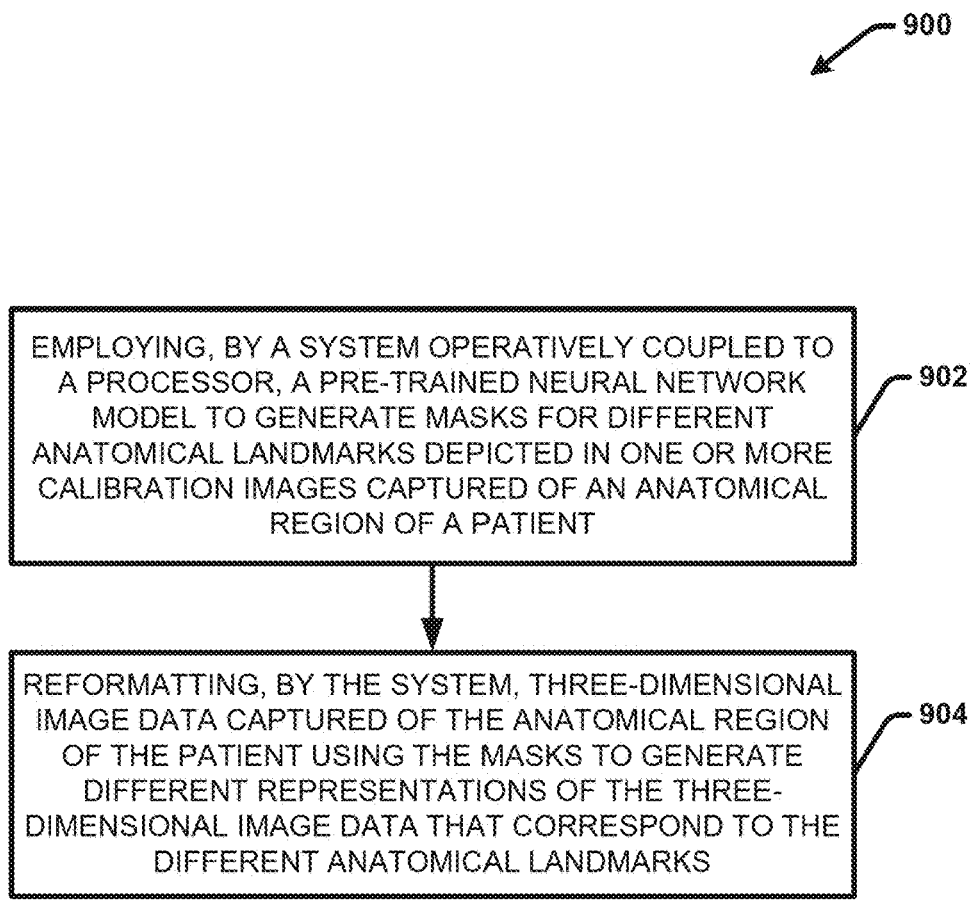
FIG. 9 presents a high-level flow diagram of an example computer-implemented process for generating reformatted views of a 3D anatomy scan using scan prescription masks in accordance with one or more embodiments of the disclosed subject matter.

FIG. 9 presents a high-level flow diagram of an example computer-implemented process 900 for generating reformatted views of a 3D anatomy scan using scan prescription masks in accordance with one or more embodiments of the disclosed subject matter. Repetitive description of like elements employed in respective embodiments is omitted for sake of brevity.

In accordance with process 900, at 902 a system operatively coupled to a processor (e.g., system 100, system 800, or the like), can employ a pre-trained neural network model (e.g., one or more deep-learning networks 108) to generate masks for different anatomical landmarks depicted in one or more calibration images (e.g., provided by the calibration data 102) captured of an anatomical region of a patient (e.g., using mask generation component 106). At 904, the system can reformat 3D image data (e.g., 3D image data 112) captured of the anatomical region of the patient using the masks to generate different representations of the 3D image data that correspond to (or are otherwise aligned with) the different anatomical landmarks (e.g., using reformatting component 114).

Figure 10:
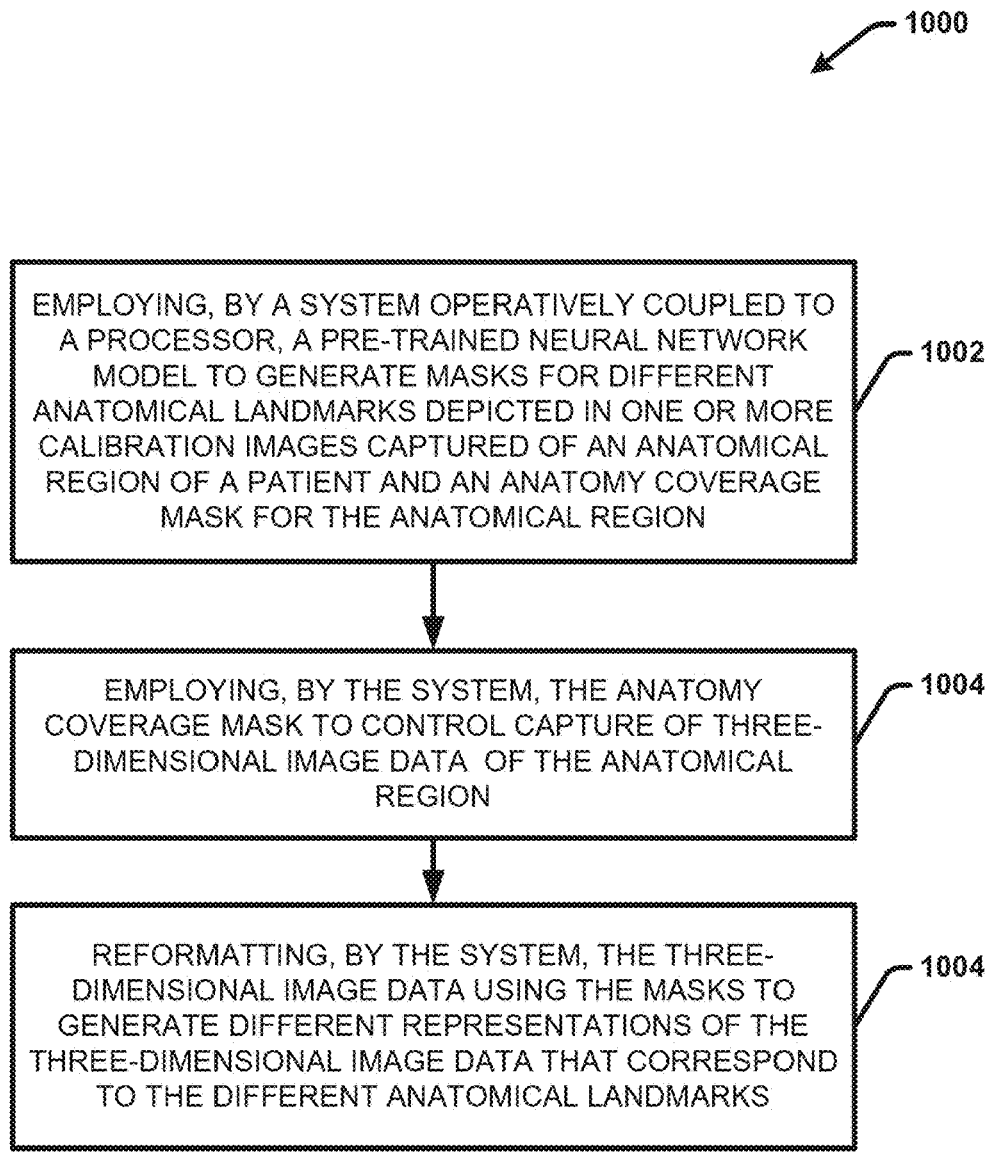
FIG. 10 presents a high-level flow diagram of an example computer-implemented process for generating reformatted views of a 3D anatomy scan using scan prescription masks in accordance with one or more embodiments of the disclosed subject matter.

FIG. 10 presents a high-level flow diagram of an example computer-implemented process 1000 for generating reformatted views of a 3D anatomy scan using scan prescription masks in accordance with one or more embodiments of the disclosed subject matter. Repetitive description of like elements employed in respective embodiments is omitted for sake of brevity.

In accordance with process 1000, at 1002 a system operatively coupled to a processor (e.g., system 100, system 800, or the like), can employ a pre-trained neural network model (e.g., one or more deep-learning networks 108) to generate masks for different anatomical landmarks depicted in one or more calibration images (e.g., provided by the calibration data 102) captured of an anatomical region of a patient an anatomy coverage mask of the anatomical region (e.g., using mask generation component 106). At 1004, the system can employ the anatomy coverage mask to control capture of 3D image data of the anatomical region (e.g., via acquisition control unit 802). At 1006, the system can reformat the 3D image data (e.g., 3D image data 112) using the masks to generate different representations of the 3D image data that correspond to (or are otherwise aligned with) the different anatomical landmarks (e.g., using reformatting component 114).

Figure 11:
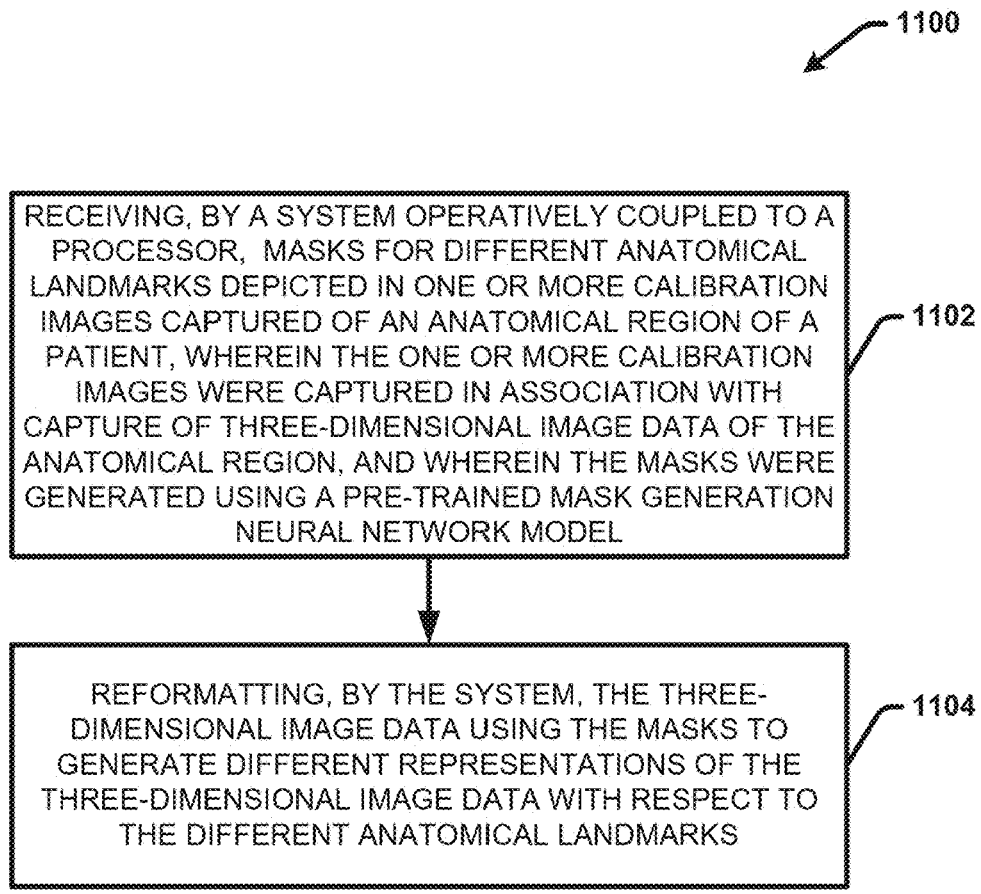
FIG. 11 presents a high-level flow diagram of another example computer-implemented process for generating reformatted views of a 3D anatomy scan using scan prescription masks in accordance with one or more embodiments of the disclosed subject matter.

FIG. 11 presents a high-level flow diagram of another example computer-implemented process 1100 for generating reformatted views of a 3D anatomy scan using scan prescription masks in accordance with one or more embodiments of the disclosed subject matter. Repetitive description of like elements employed in respective embodiments is omitted for sake of brevity.

In accordance with process 1100, at 1102 a system operatively coupled to a processor (e.g., system 100, system 800, or the like), can receive e masks for different anatomical landmarks depicted in one or more calibration images (e.g., provided by the calibration data 102) captured of an anatomical region of a patient (e.g., using mask generation component 106), wherein the one or more calibration images were captured in association with 3D image data (e.g., 3D image data 112) of the anatomical region of the anatomical region, and wherein the masks ger generating using a pre-trained mask generation neural network model (e.g., one or more deep-learning networks 108). At 1104, the system can reformat the 3D image data using the masks to generate different representations of the 3D image data with respect to (or are otherwise aligned with) the different anatomical landmarks (e.g., using reformatting component 114).

Figure 12:
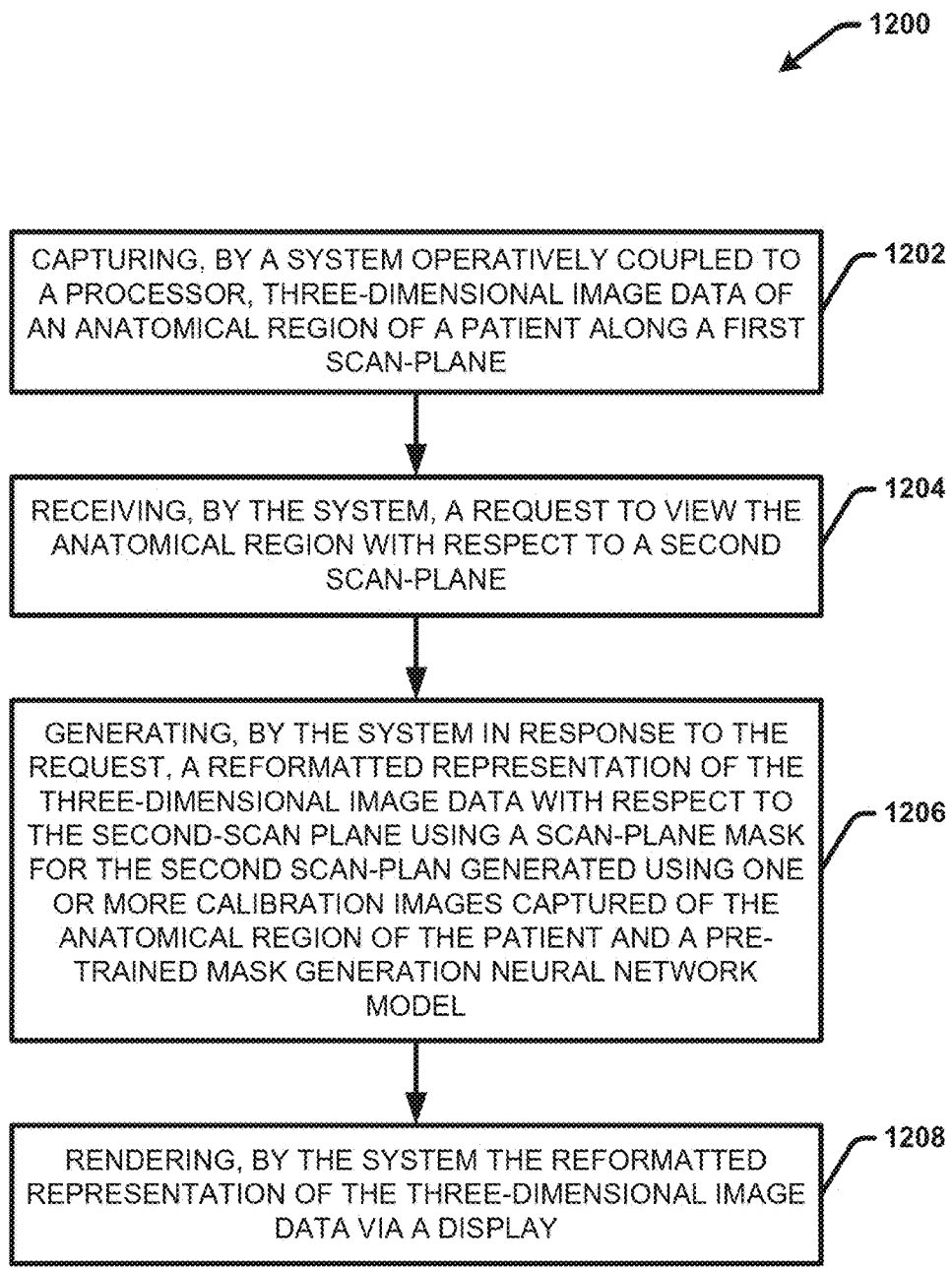
FIG. 12 presents a high-level flow diagram of another example computer-implemented process for generating reformatted views of a 3D anatomy scan using scan prescription masks in accordance with one or more embodiments of the disclosed subject matter.

FIG. 12 presents a high-level flow diagram of another example computer-implemented process 1200 for generating reformatted views of a 3D anatomy scan using scan prescription masks in accordance with one or more embodiments of the disclosed subject matter. Repetitive description of like elements employed in respective embodiments is omitted for sake of brevity.

In accordance with process 1200, at 1202 a system operatively coupled to a processor (e.g., system 800, or the like), can capture 3D image data of an anatomical region of a patient captured along a first scan-plane (e.g., via the medical image scanning device 804). At 1204, the system can receive a request to view the anatomical region with respect to a second scan-plane (e.g., via the rendering component 808). At 1206, in response to the request, the system can generate (e.g., using reformatting component 114) a reformatted representation of the 3D image data with respect to the second-scan plane using a scan-plane mask (e.g., included in the masked calibration data 110) for the second scan-plan generated using one or more calibration images captured of the anatomical region of the patient and a pre-trained mask generation neural network model (e.g., one or more deep-learning networks 108). At 1208, the system can render the reformatted representation of the 3D image data via a display (e.g., display 816 using rendering component 814).

Figure 13:
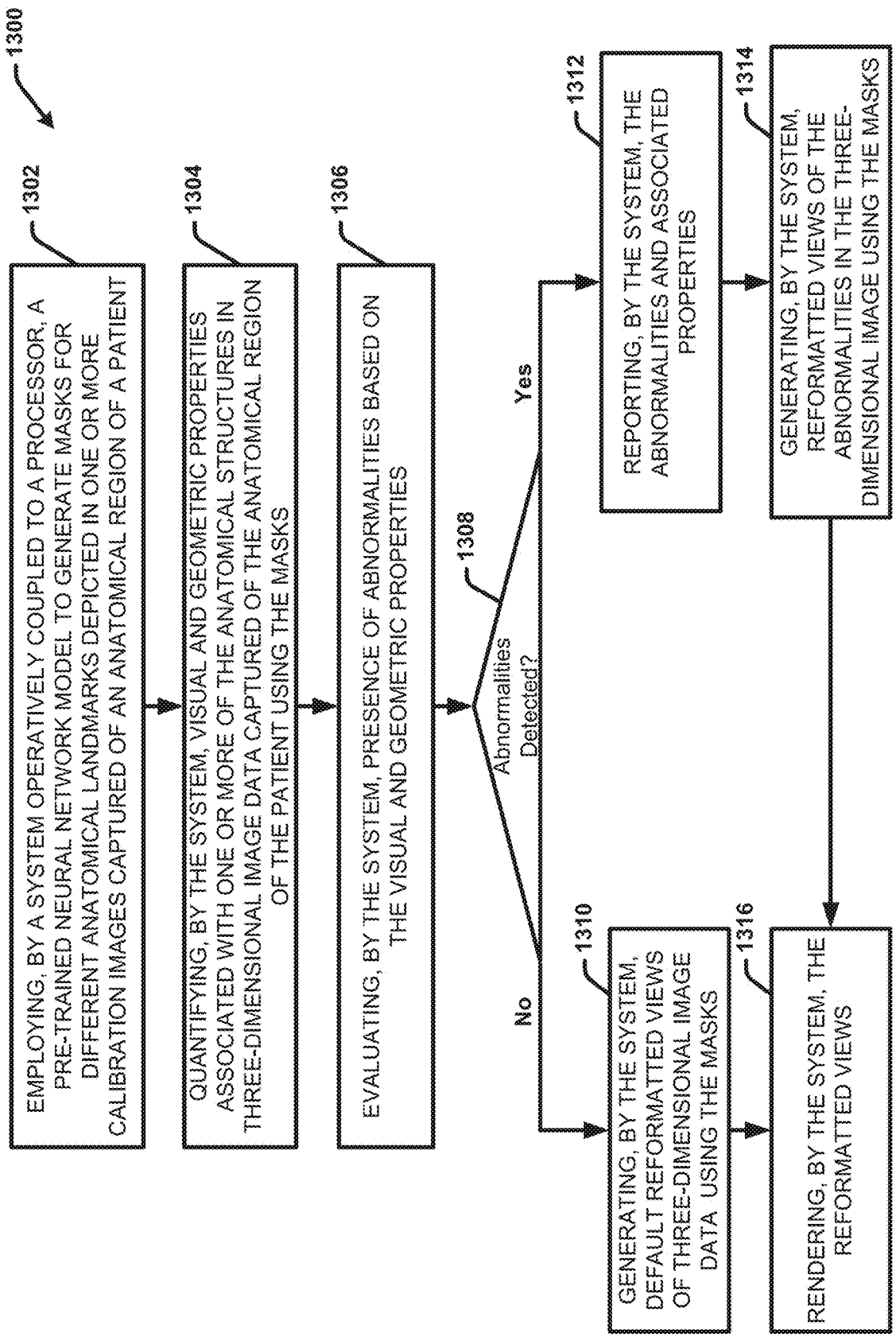
FIG. 13 presents a high-level flow diagram of another example computer-implemented process for generating reformatted views of a 3D anatomy scan using scan prescription masks in accordance with one or more embodiments of the disclosed subject matter.

FIG. 13 presents a high-level flow diagram of another example computer-implemented process 1300 for generating reformatted views of a 3D anatomy scan using scan prescription masks in accordance with one or more embodiments of the disclosed subject matter. Repetitive description of like elements employed in respective embodiments is omitted for sake of brevity.

In accordance with process 1300, at 1302 a system operatively coupled to a processor (e.g., system 100, system 800, or the like), can employ a pre-trained neural network model (e.g., one or more pre-trained deep learning networks 108) to generate masks (e.g., via mask generation component 106) for different anatomical landmarks depicted in one or more calibration images captured of an anatomical region of a patient. At 1304, the system can quantify visual and geometric properties associated with one or more of the anatomical structures in 3D image data captured of the anatomical region of the patient using the masks (e.g., via quantification component 116). For example, the quantification component 116 can determine relative geometrical sizes, shapes and positions of the one or more anatomical structures as well as visual properties of the 3D image data defined by the masks (e.g., touristy, coloration, pattern recognition, etc.). At 1306, the system can evaluate presence of abnormalities based on the visual and geometric properties (e.g., using anomaly detection component 118). For example, the anomaly detection component 118 can employ one or more anomaly detection models (e.g., machine learning models) configured to detect defined anomalies indicative of a medical condition or illness as well as undefined anomalies indicative of unusual geometric and/or visual properties (e.g., relative to previous imaging studies for the patient and/or imaging studies for other patients).

At 1308, the system can determine whether any anomalies were detected (e.g., via the anomaly detection component 118). If at 1308, no anomalies were detected, then at 1310, the system can generate default reformatted views of the 3D image data using the masks. For example, the default reformatted view may include a defined set of different relevant views of the anatomical region of interest. At 1316, the system can further render the reformatted views (e.g., via rendering component 814 and display 816) to a reviewer (e.g., a radiologist, a technician, etc.) in association with usage of a medical imaging visualization application or the like). However, if at 1308, one or more anomalies were detected, then at 1312, the system can report the anomalies and their associated properties (e.g., the geometric and/or visual properties for which the anomalies were characterized) using a suitable electronic reporting mechanism (e.g., via a notification message displayed/associated with the patient imaging study as rendered via a medical imaging visualization application). At 1314, the system may further generate reformatted views the anomalies in the 3D image data using the masks (e.g., via reformatting component 114). For example, the reformatting component may generate specialized reformatted views of the anatomical structure or structures associated with a detected anomaly in addition to and/or in alternative to the default reformatted views. At 1316, the system can further render the reformatted view (e.g., the specialized and/or the default reformatted views).

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 14, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 14:
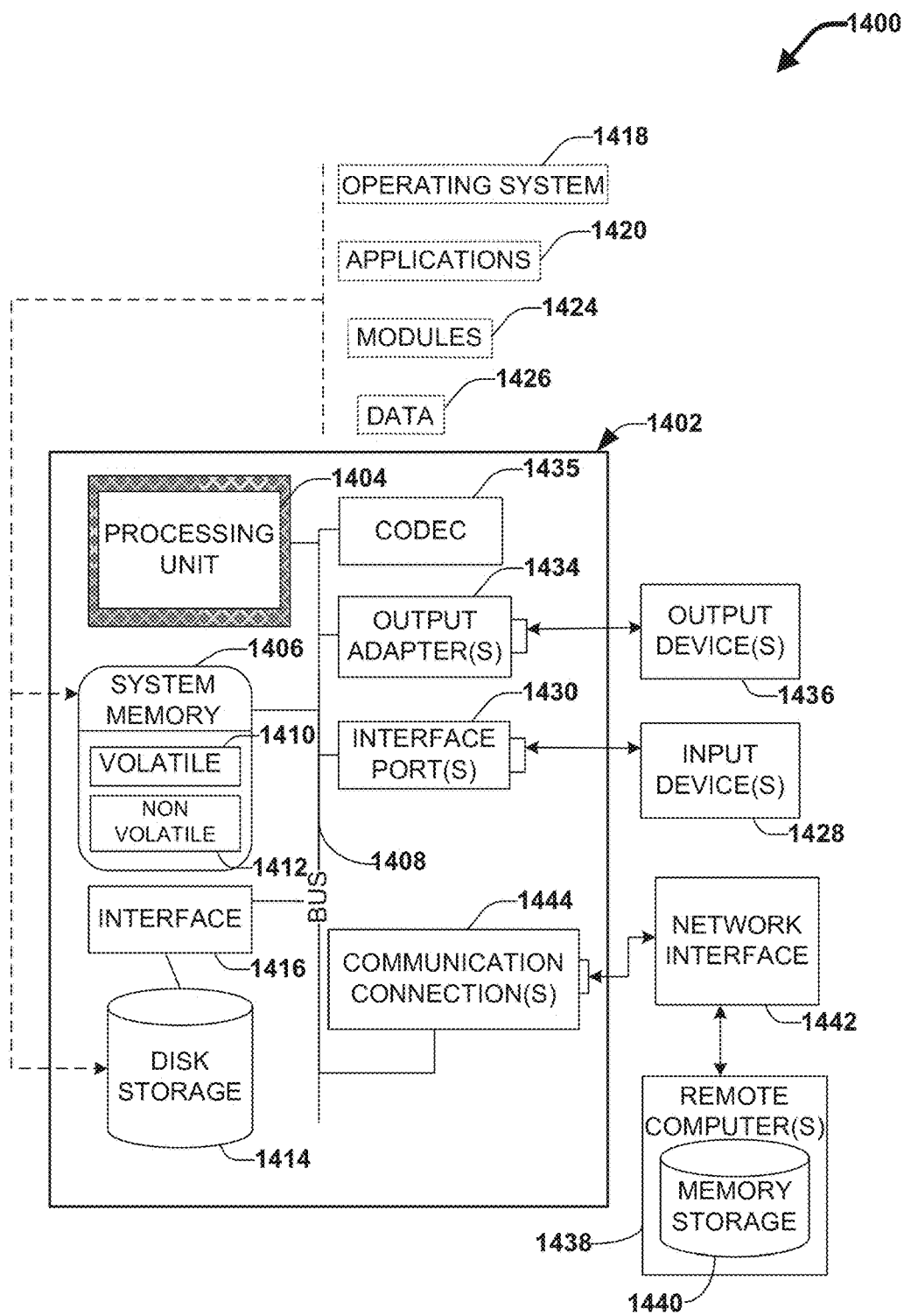
FIG. 14 illustrates a block diagram of an example, non-limiting operating environment in which one or more embodiments described herein can be facilitated.

With reference to FIG. 14, an example environment 1400 for implementing various aspects of the claimed subject matter includes a computer 1402. The computer 1402 includes a processing unit 1404, a system memory 1406, a codec 1435, and a system bus 1408. The system bus 1408 couples system components including, but not limited to, the system memory 1406 to the processing unit 1404. The processing unit 1404 can be any of various available processors. Dual microprocessors and other multiprocessor architectures also can be employed as the processing unit 1404.

The system bus 1408 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1406 includes volatile memory 1410 and non-volatile memory 1412, which can employ one or more of the disclosed memory architectures, in various embodiments. The basic input/output system (BIOS), containing the basic routines to transfer information between elements within the computer 1402, such as during start-up, is stored in non-volatile memory 1412. In addition, according to present innovations, codec 1435 can include at least one of an encoder or decoder, wherein the at least one of an encoder or decoder can consist of hardware, software, or a combination of hardware and software. Although, codec 1435 is depicted as a separate component, codec 1435 can be contained within non-volatile memory 1412. By way of illustration, and not limitation, non-volatile memory 1412 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1412 can employ one or more of the disclosed memory devices, in at least some embodiments. Moreover, non-volatile memory 1412 can be computer memory (e.g., physically integrated with computer 1402 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1410 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1402 can also include removable/non-removable, volatile/non-volatile computer storage medium. FIG. 14 illustrates, for example, disk storage 1414. Disk storage 1414 includes, but is not limited to, devices like a magnetic disk drive, solid state disk (SSD), flash memory card, or memory stick. In addition, disk storage 1414 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1414 to the system bus 1408, a removable or non-removable interface is typically used, such as interface 1416. It is appreciated that disk storage 1414 can store information related to a user. Such information might be stored at or provided to a server or to an application running on a user device. In one embodiment, the user can be notified (e.g., by way of output device(s) 1436) of the types of information that are stored to disk storage 1414 or transmitted to the server or application. The user can be provided the opportunity to opt-in or opt-out of having such information collected or shared with the server or application (e.g., by way of input from input device(s) 1428).

It is to be appreciated that FIG. 14 describes software that acts as an intermediary between users and the basic computer resources described in the suitable operating environment 1400. Such software includes an operating system 1418. Operating system 1418, which can be stored on disk storage 1414, acts to control and allocate resources of the computer 1402. Applications 1420 take advantage of the management of resources by operating system 1418 through program modules 1424, and program data 1426, such as the boot/shutdown transaction table and the like, stored either in system memory 1406 or on disk storage 1414. It is to be appreciated that the claimed subject matter can be implemented with various operating systems or combinations of operating systems.

A user enters commands or information into the computer 1402 through input device(s) 1428. Input devices 1428 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1404 through the system bus 1408 via interface port(s) 1430. Interface port(s) 1430 include, for example, a serial port, a parallel port, a game port, and a universal serial bus (USB). Output device(s) 1436 use some of the same type of ports as input device(s) 1428. Thus, for example, a USB port can be used to provide input to computer 1402 and to output information from computer 1402 to an output device 1436. Output adapter 1434 is provided to illustrate that there are some output devices 1436 like monitors, speakers, and printers, among other output devices 1436, which require special adapters. The output adapters 1434 include, by way of illustration and not limitation, video and sound cards that provide a means of connection between the output device 1436 and the system bus 1408. It should be noted that other devices or systems of devices provide both input and output capabilities such as remote computer(s) 1438.

Computer 1402 can operate in a networked environment using logical connections to one or more remote computers, such as remote computer(s) 1438. The remote computer(s) 1438 can be a personal computer, a server, a router, a network PC, a workstation, a microprocessor based appliance, a peer device, a smart phone, a tablet, or other network node, and typically includes many of the elements described relative to computer 1402. For purposes of brevity, only a memory storage device 1440 is illustrated with remote computer(s) 1438. Remote computer(s) 1438 is logically connected to computer 1402 through a network interface 1442 and then connected via communication connection(s) 1444. Network interface 1442 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1444 refers to the hardware/software employed to connect the network interface 1442 to the bus 1408. While communication connection 1444 is shown for illustrative clarity inside computer 1402, it can also be external to computer 1402. The hardware/software necessary for connection to the network interface 1442 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a mask generation component that employs a pre-trained neural network model to generate masks for different anatomical landmarks depicted in one or more calibration images captured of an anatomical region of a patient; and
a reformatting component that reformats three-dimensional image data captured of the anatomical region of the patient using the masks to generate different representations of the three-dimensional image data that correspond to the different anatomical landmarks, wherein the different representations comprise at least one of synthetic two-dimensional images generated from the three-dimensional image data or synthetic three-dimensional images generated from the three-dimensional image data.

2. The system of claim 1, wherein the masks respectively provide an anatomical frame of reference for the different anatomical landmarks as depicted in the three-dimensional image data.

3. The system of claim 1, wherein the masks include an anatomy coverage mask defining a three-dimensional region of interest for the anatomical region and wherein the three-dimensional image data was captured within the three-dimensional region of interest using the anatomy coverage mask.

4. The system of claim 1, wherein the three-dimensional image data was captured along a first scan plane, wherein different anatomical landmarks comprise one or more second scan planes that are different than the first scan plan, and wherein the different representations provide perspectives of the three-dimensional image data generated from the one or more second scan planes.

5. The system of claim 1, wherein the different anatomical landmarks comprise one or more anatomical structures and wherein the different representations provide perspectives of the three-dimensional image data relative to the one or more anatomical structures.

6. The system of claim 1, wherein the different anatomical landmarks comprise a non-planar anatomical structure.

7. The system of claim 6, wherein the masks comprise a non-planar mask corresponding to the non-planar anatomical structure and wherein the reformatting component generates a planar representation of the non-planar anatomical structure using the three-dimensional image data and the non-planar mask.

8. The system of claim 1, wherein the one or more calibration images have a lower resolution relative to the three-dimensional image data.

9. The system of claim 1, wherein the one or more calibration images comprise one or more localizer images or coil sensitivity images.

10. The system of claim 1, further comprising:
a rendering component that renders the different representations via a display.

11. The system of claim 1, wherein the computer executable components further compromise:
a quantification component that quantifies one or more geometric or visual properties associated with one or more of the different anatomical landmarks using the masks and the three-dimensional image data; and
an anomaly detection component that evaluates presence of one or more anomalies associated with the one or more of the different anatomical landmarks based on the one or more geometric and visual properties using machine learning and artificial intelligence techniques.

12. A method comprising:
employing, by a system operatively coupled to a processor, a pre-trained neural network model to generate masks for different anatomical landmarks depicted in one or more calibration images captured of an anatomical region of a patient; and reformatting, by the system, three-dimensional image data captured of the anatomical region of the patient using the masks to generate different representations of the three-dimensional image data that correspond to the different anatomical landmarks, wherein the different representations comprise at least one of synthetic two-dimensional images generated from the three-dimensional image data or synthetic three-dimensional images generated from the three-dimensional image data.

13. The method of claim 12, wherein the masks respectively provide an anatomical frame of reference for the different anatomical landmarks as depicted in the three-dimensional image data.

14. The method of claim 12, wherein the three-dimensional image data was captured along a first scan plane, wherein different anatomical landmarks comprise one or more second scan planes that are different than the first scan plan, and wherein the different representations provide perspectives of the three-dimensional image data generated from the one or more second scan planes.

15. The method of claim 12, wherein the different anatomical landmarks comprise one or more anatomical structures and wherein the different representations provide perspectives of the three-dimensional image data relative to the one or more anatomical structures.

16. The method of claim 12, wherein the different anatomical landmarks comprise a non-planar anatomical structure.

17. The method of claim 12, wherein the masks comprise a non-planar mask corresponding to the non-planar anatomical structure and wherein the reformatting component generates a planar representation of the non-planar anatomical structure using the three-dimensional image data and the non-planar mask.

18. A machine-readable storage medium, comprising executable instructions that, when executed by a processor, facilitate performance of operations, comprising:
  employing a pre-trained neural network model to generate masks for different anatomical landmarks depicted in one or more calibration images captured of an anatomical region of a patient; and
  reformatting three-dimensional image data captured of the anatomical region of the patient using the masks to generate different representations of the three-dimensional image data that correspond to the different anatomical landmarks, wherein the different representations comprise at least one of synthetic two-dimensional images generated from the three-dimensional image data or synthetic three-dimensional images generated from the three-dimensional image data.

19. The machine-readable storage medium of claim 18, wherein the three-dimensional image data was captured along a first scan plane, wherein different anatomical landmarks comprise one or more second scan planes that are different than the first scan plan, and wherein the different representations provide perspectives of the three-dimensional image data generated from the one or more second scan planes.

20. The machine-readable storage medium of claim 18, wherein the masks include an anatomy coverage mask defining a three-dimensional region of interest for the anatomical region and wherein the three-dimensional image data was captured within the three-dimensional region of interest using the anatomy coverage mask.

* * * * *